(12) United States Patent
Grill et al.

(10) Patent No.: US 11,369,796 B2
(45) Date of Patent: Jun. 28, 2022

(54) SYSTEMS AND METHODS FOR OPTIMIZED WAVEFORM NEURAL BLOCK

(71) Applicant: Duke University, Durham, NC (US)

(72) Inventors: Warren Grill, Durham, NC (US); Nikki Pelot, Durham, NC (US); Timothy Hoer, Durham, NC (US)

(73) Assignee: Duke University, Durham, NC (US)

( * ) Notice: Subject to any disclaimer, the term of this patent is extended or adjusted under 35 U.S.C. 154(b) by 157 days.

(21) Appl. No.: 16/651,231

(22) PCT Filed: Sep. 25, 2018

(86) PCT No.: PCT/US2018/052652
§ 371 (c)(1),
(2) Date: Mar. 26, 2020

(87) PCT Pub. No.: WO2019/067446
PCT Pub. Date: Apr. 4, 2019

(65) Prior Publication Data
US 2020/0330767 A1    Oct. 22, 2020

Related U.S. Application Data

(60) Provisional application No. 62/563,687, filed on Sep. 27, 2017.

(51) Int. Cl.
*A61N 1/36* (2006.01)
*G16H 20/30* (2018.01)
(Continued)

(52) U.S. Cl.
CPC ....... *A61N 1/36171* (2013.01); *A61N 1/3615* (2013.01); *A61N 1/36071* (2013.01);
(Continued)

(58) Field of Classification Search
CPC .......... A61N 1/18; A61N 1/32; A61N 1/3606; A61N 1/36071; A61N 1/36139;
(Continued)

(56) References Cited

U.S. PATENT DOCUMENTS 7,389,145 B2   6/2008   Kilgore et al.
9,089,708 B2   7/2015   Grill et al.
(Continued)

OTHER PUBLICATIONS

International Search Report and Written Opinion for PCT/US18/52652, dated Feb. 12, 2019. 19 pages.

*Primary Examiner* — George Manuel
(74) *Attorney, Agent, or Firm* — Casimir Jones, S.C.; Peter J. Schlueter

(57) ABSTRACT

The present disclosure provides systems and methods relating to neuromodulation. In particular, the present disclosure provides systems and methods for identifying optimized waveforms for blocking neural conduction. The systems and methods of neuromodulation disclosed herein facilitate the treatment of various diseases associated with pathological neural activity. The optimized waveforms for blocking neural conduction are identified through use of a global optimization algorithm based on predetermined performance criteria. A plurality of waveforms are generated and evaluated for neuronal conduction block using a computational model of extracellular neuronal stimulation, and at least on candidate waveform having an optimized shape capable of blocking neural conduction is identified.

17 Claims, 24 Drawing Sheets

(51) Int. Cl.
*G16H 50/50* (2018.01)
*A61N 1/378* (2006.01)

(52) U.S. Cl.
CPC .............. *A61N 1/378* (2013.01); *G16H 20/30* (2018.01); *G16H 50/50* (2018.01)

(58) Field of Classification Search
CPC .............. A61N 1/36146; A61N 1/3615; A61N 1/36171; A61N 1/378; G16H 20/30; G16H 50/50; G16H 50/70
See application file for complete search history.

(56) References Cited

U.S. PATENT DOCUMENTS

2004/0127953 A1* 7/2004 Kilgore .............. A61N 1/36071
  607/46
2007/0156200 A1  7/2007 Kornet et al.
2011/0160795 A1* 6/2011 Osorio .................. A61B 5/369
  607/45

* cited by examiner

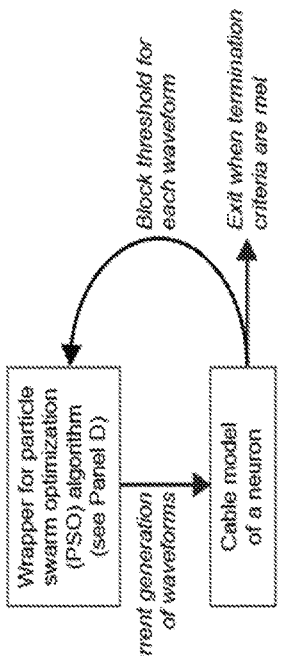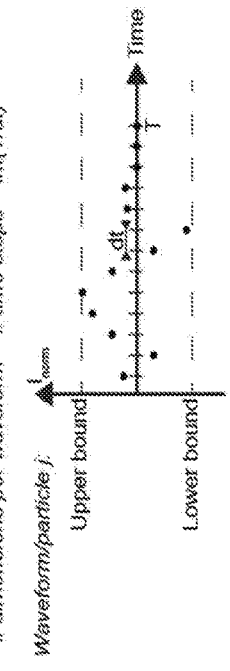
FIGS. 1A-1D

Optimization Algorithms

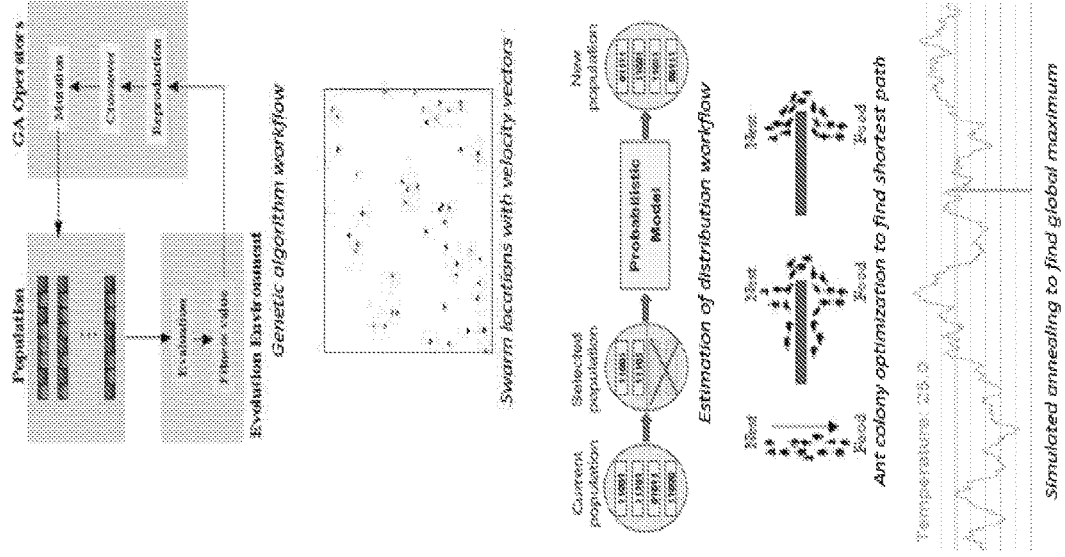

- Genetic Algorithm (GA)
  - Method: simulates evolutionary mechanisms to operate on individuals composed of "genes," or variables for optimization
  - Parameters: methods of selection, recombination (crossover, mutation), pop. size, seeding
    - Options: elitism, number of parents, islands of interaction, immigrants, etc.
  - Pros: intuitive, popular for systems with large number of variables
  - Cons: many parameters to manipulate, long convergence time
  - Concerns: efficiency/slow convergence, meaningful recombination

- Particle Swarm Optimization (PSO)
  - Method: simulates simplified social system, e.g. a flock of birds, with particles flying through solution space in D-dimensions/variables
  - Parameters: connectivity/topology, inertial weighting, influence weighting, initialization
    - Options: replacement of poor performing agents
  - Pros: easy to implement, good global exploration, often faster convergence, higher quality solutions than GA
  - Cons: must carefully manipulate parameters to avoid flying past good solutions or getting stuck in local minima
  - Concerns: can only evaluate fitness of complete waveform — how to best evaluate fitness of a particle in single dimension? How does waveform translate to D-dimensions?

- Estimation of Distribution Algorithm (EDA) – "Competent GA"
  - Method: attempts to learn the relationship between variables to incrementally improve a probabilistic model from which new candidates are created
  - Parameters: learning, selection, seeding, replacement methods, probabilistic model
    - Optional: repairing method (to operate on generated solutions)
  - Pros: good for problems with high epistasis, high dimensionality – performs better than GA when no dependencies between variables
  - Cons: time complexity of learning model, limited global exploration
  - Concerns: complicated implementation

- Ant Colony Optimization (ACO)
  - Method: uses probabilistic model based on previous successes to produce directed graph solutions, simulating behavior of ants
  - Parameters: pheromone reinforcement/evaporation, graph size, pheromone-heuristic decision weighting, pheromone matrix initialization
  - Pros: simple implementation
  - Cons: typically used for shortest path optimization, discrete search space
  - Concerns: helps constrain waveform, but solution space must be discrete

- Simulated Annealing (SA)
  - Method: probabilistically decides between staying in state s or moving to neighboring state s', depending on the constantly decreasing global parameter temperature and the energy/fitness of states s and s'
  - Parameters: acceptance probability function (how search is constrained by temp.)
  - Pros: searches globally then locally, like PSO
  - Cons: search requires fitness of neighboring state, discrete search space

FIG. 24

SYSTEMS AND METHODS FOR OPTIMIZED WAVEFORM NEURAL BLOCK

RELATED APPLICATIONS

This application claims priority to and the benefit of U.S. Provisional Patent Application No. 62/563,687 filed Sep. 27, 2017, which is incorporated herein by reference in its entirety for all purposes.

GOVERNMENT FUNDING

This invention was made with Government support under Federal Grant No. NIH OT2 OD025340 awarded by National Institutes of Health. The Federal Government has certain rights to the invention.

FIELD

The present disclosure provides systems and methods relating to neuromodulation. In particular, the present disclosure provides systems and methods for identifying optimized waveforms for blocking neural conduction. The systems and methods of neuromodulation disclosed herein facilitate the treatment of various diseases associated with pathological neural activity.

BACKGROUND

Treating diseases by delivering electrical signals to the nervous system to modulate its activity is conventionally achieved by eliciting action potentials (e.g., electrical stimulation, electrical activation, or electrical excitation). However, a full spectrum of effective neuromodulatory therapies also requires the capability to block pathological—or otherwise unwanted—neural activity. Current approaches for producing neural block with electrical signals include direct current (DC) and kilohertz frequency (KHF) signals. However, the charge imbalance of DC block (i.e., injecting net charge into the tissue) poses significant risk of tissue damage and/or electrode breakdown. KHF electrical signals have been applied to the spinal cord to treat chronic pain, to peripheral somatosensory nerves to treat phantom limb pain, and to the subdiaphragmatic vagus nerves to treat obesity, among other applications. However, in clinical applications, the high energy demands of KHF electrical signals reduce the lifetime of primary cell implantable pulse generators (IPGs) and increase the size and/or recharge frequency of rechargeable IPGs. Frequent recharging of rechargeable batteries (e.g., every few days) requires patient compliance and reminds the patient of their condition, while replacement surgery of primary cell batteries (e.g., every few years) is costly and involves the typical risks associated with surgery, including infection. Furthermore, higher energy waveforms may also increase the risk of tissue damage, which remains a concern with conventional high-amplitude sinusoidal or rectangular biphasic waveforms used for block. In addition, KHF block is associated with an "onset response." That is, upon starting the KHF signal, there is a transient burst of nerve activity (action potentials) before the neural element enters a blocked state, and this onset response can cause undesirable side effects. Therefore, there is a clear need to optimize the performance of electrical signals for production of block of neural activity.

Development of effective, efficient, and selective neural block requires exploration and understanding of a large multi-dimensional parameter space, including waveform shape, amplitude, and frequency. Additionally, optimal or even appropriate electrical signals may vary across nerve fiber types. Computational models, especially those that represent the anatomical, morphological, and biophysical properties of the nerve fibers of interest, enable efficient exploration of this parameter space and rigorous optimization of application-specific parameters. Current methods for selecting waveform parameters (i.e., programming the neural stimulation devices) are crude, particularly for KHF devices. KHF therapies generally use a fixed waveform and frequency, and the amplitude is set either by the physician or a company representative during a short appointment. The amplitude is generally set as high as possible without patient discomfort.

SUMMARY

Embodiments of the present disclosure include a method of identifying an optimized waveform shape for blocking neural conduction. In accordance with these embodiments, the method includes generating a plurality of waveforms using a global optimization algorithm based on predetermined performance criteria, evaluating the plurality of waveforms for neuronal conduction block using a computational model of extracellular neuronal stimulation, and identifying at least one candidate waveform having an optimized shape capable of blocking neural conduction.

In some embodiments of the method, the global optimization algorithm includes at least one of a genetic algorithm, a particle swarm algorithm, a simulated annealing algorithm, an ant colony algorithm, an estimation of distribution algorithm, and any combinations and derivations thereof.

In some embodiments of the method, the predetermined performance criteria are incorporated into a cost function used to evaluate the fitness of the plurality of waveforms. In accordance with these embodiments, the predetermined performance criteria include at least one of: minimizing energy required for conduction block, minimizing power required for conduction block, minimizing charge imbalance in the optimized waveform, minimizing onset response produced when the optimized waveform is turned on, maximizing degree of conduction block, minimizing voltage or current required for conduction block with the optimized waveform, maximizing therapeutic benefit produced by application of the optimized waveform, minimizing adverse effect produced by application of the optimized waveforms, maximizing selectivity of block between nerve fiber types blocked by application of the optimized waveform, maximizing selectivity of block between nerve fiber diameters blocked by application of the optimized waveform, maximizing selectivity between nerve fiber locations blocked by application of the optimized waveform, and any combinations and derivatives thereof.

In some embodiments of the method, the predetermined performance criteria include minimizing the onset response produced when the optimized waveform is turned on and maximizing selectivity of block between nerve fiber types blocked by application of the optimized waveform, maximizing selectivity between nerve fiber diameters blocked by application of the optimized waveform, and/or maximizing selectivity of block between nerve fiber locations blocked by application of the optimized waveform.

In some embodiments of the method, the predetermined performance criteria include maximizing the degree of neural conduction block, minimizing charge imbalance in the optimzed waveform, and/or minimizing power required for conduction block.

In some embodiments of the method, the computational model of extracellular neuronal stimulation is coupled to the global optimization algorithm based on the predetermined performance criteria. In some embodiments, the computational model includes a model of an A-type myelinated axon, a model of a B-type myelinated axon, a model of a C-type unmyelinated axon, a model of a presynaptic terminating axon, a model of a neuron comprising representations of the dendrites, cell body, and axon, or components thereof, or a model of an afferent neuron or an efferent neuron.

In some embodiments of the method, the candidate waveform is monophasic. In some embodiments, the candidate waveform is multiphasic, or biphasic. In some embodiments, the candidate waveform is charge-balanced.

In some embodiments of the method, the candidate waveform blocks neural conduction at a waveform repetition frequency from about 1 to about 100 kHz.

In some embodiments of the method, the global optimization algorithm is a particle swarm optimization (PSO) algorithm. In accordance with these embodiments, a minimum swarm energy of the PSO algorithm varies less than about 0.1% to about 10.0% over from about 10 generations to about 100 generations after generating a minimum number of generations, or minimum and maximum waveform energies in the swarm at a given generation are less than 10% apart after generating a minimum number of generations, or any combinations thereof.

In some embodiments of the method, the shape of the optimized waveform minimizing the energy required for conduction block comprises a higher, narrower anodic phase and a shallower, broader cathodic phase. In some embodiments of the method, the shape of the optimized waveform is based on a sum of sinusoidal functions, a sum of Gaussian functions, or any combinations and derivations thereof.

In some embodiments of the method, the shape of the optimized waveform minimizing the energy required for conduction block comprises a higher, narrower anodic phase and a shallower, broader cathodic phase. In some embodiments of the method, the shape of the optimized waveform is based on a sum of sinusoidal functions, a sum of Gaussian functions, a sum of polynomial functions, or a sum or ratio of any other functional forms, as would be recognized by one of ordinary skill in the art based on the present disclosure.

In some embodiments of the method, the minimum energy of the candidate waveform is from about 9.0 pJ/$\Omega$ to about 20.0 pJ/$\Omega$ for one period at about 5 kHz to about 20 kHz. In some embodiments of the method, the minimum energy of the candidate waveform is from about 3.0 pJ/$\Omega$ to about 80.0 pJ/$\Omega$ for one period at about 5 kHz to about 20 kHz dependent on the distance from the electrode to the nerve fibers being blocked and the diameter of the nerve fibers being blocked.

Embodiments of the present disclosure also include a system for blocking neural conduction. In accordance with these embodiments, the system includes an electrode sized and configured for implantation in proximity to neural tissue, and a pulse generator coupled to the electrode, the pulse generator including a power source comprising a battery and a microprocessor coupled to the battery, wherein the pulse generator is capable of applying to the electrode a stimulation waveform having an optimized shape capable of blocking neural conduction.

In some embodiments of the system, the stimulation waveform shape is optimized to meet performance criteria that include at least one of: minimizing energy required for conduction block, minimizing power required for conduction block, minimizing charge imbalance in the optimized waveform, minimizing onset response produced when the optimized waveform is turned on, maximizing degree of conduction block, minimizing voltage or current required for conduction block with the optimized waveform, maximizing therapeutic benefit produced by application of the optimized waveform, minimizing adverse effect produced by application of the optimized waveforms, maximizing selectivity between nerve fiber types blocked by application of the optimized waveform, maximizing selectivity between nerve fiber diameters blocked by application of the optimized waveform, maximizing selectivity between nerve fiber locations blocked by application of the optimized waveform, and any combinations and derivatives thereof.

In some embodiments of the system, the stimulation waveform has an optimized shape capable of blocking neural conduction with minimum energy.

In some embodiments of the system, the stimulation waveform blocks neural conduction at a waveform repetition frequency from about 1 to about 100 kHz.

In some embodiments of the system, the energy-optimized shape of the candidate waveform comprises a higher, narrower anodic phase and a shallower, broader cathodic phase. In some embodiments of the system, the shape of the optimized waveform is based on a sum of sinusoidal functions, a sum of Gaussian functions, or any combinations and derivations thereof.

In some embodiments of the system, the minimum energy of the candidate waveform is from about 9.0 pJ/$\Omega$ to about 20.0 pJ/$\Omega$ for one period at about 5 kHz to about 20 kHz.

Embodiments of the present disclosure also include a method for blocking neural conduction using the system described above. In accordance with these embodiments, the method includes programming the pulse generator to output the stimulation waveform (e.g., on a graphical user interface (GUI)), the stimulation waveform representing a waveform having an optimized shape capable of blocking neural conduction, and setting amplitude of the stimulation waveform, wherein the stimulation waveform blocks neural conduction when delivered by the pulse generator.

In some embodiments of the method performed using the system, the stimulation waveform shape is optimized to meet performance criteria that include at least one of: minimizing energy required for conduction block, minimizing power required for conduction block, minimizing charge imbalance in the optimized waveform, minimizing onset response produced when the optimized waveform is turned on, maximizing degree of conduction block, minimizing voltage or current required for conduction block with the optimized waveform, maximizing therapeutic benefit produced by application of the optimized waveform, minimizing adverse effect produced by application of the optimized waveforms, maximizing selectivity of block between nerve fiber types blocked by application of the optimized waveform, maximizing selectivity of block between nerve fiber diameters blocked by application of the optimized waveform, maximizing selectivity of block between nerve fiber locations blocked by application of the optimized waveform, and any combinations and derivatives thereof.

In some embodiments of the method performed using the system, the stimulation waveform has an optimized shape capable of blocking neural conduction with minimum energy. In some embodiments, the stimulation waveform blocks neural conduction at a waveform repetition frequency from about 1 to about 100 kHz.

In some embodiments of the method performed using the system, the optimized shape of the candidate waveform to block with minimum energy comprises a higher, narrower anodic phase and a shallower, broader cathodic phase. In some embodiments, the shape of the optimized waveform is based on a sum of sinusoidal functions, a sum of Gaussian functions, or any combinations and derivations thereof.

BRIEF DESCRIPTION OF THE DRAWINGS

FIGS. 1A-1D include representative schematics diagrams showing one implementation of the particle swarm optimization (PSO) algorithm.

FIG. 24 includes representative illustrations of the various global optimization algorithms that can be used to identify optimized waveforms for blocking neural conduction, according to embodiments of the present disclosure.

DETAILED DESCRIPTION

Figures 2A, 2B:
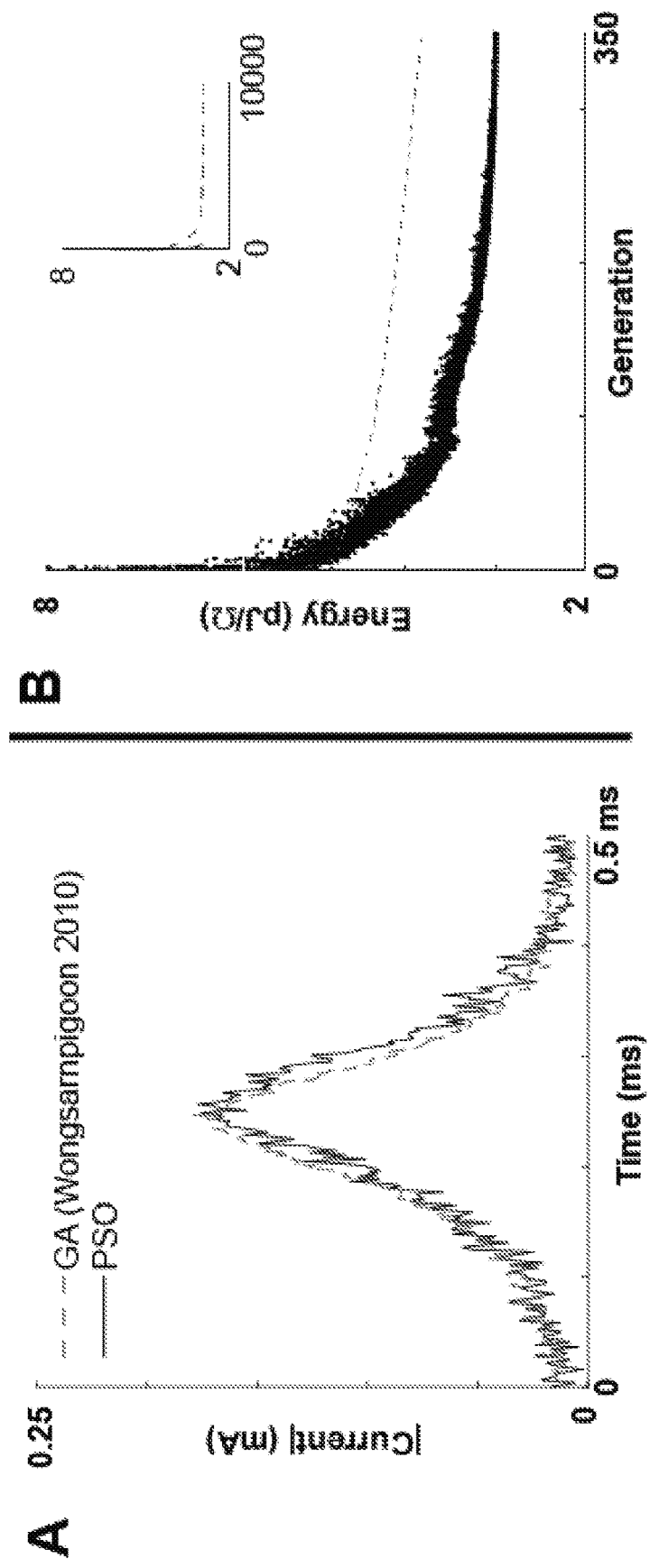
FIGS. 2A-2B include a representative optimized cathodic (monophasic) waveform with 0.5 ms pulse width for action potential initiation from a previous study using a genetic algorithm (GA) overlaid with the final waveform produced using the PSO algorithm of the present disclosure. The final waveform from GA study is averaged over five trials, while the PSO waveform is from a single trial. B: Pulse energy for waveforms produced in the GA study and by the PSO.

The present disclosure provides systems and methods relating to neuromodulation. In particular, the present disclosure provides systems and methods for identifying optimized waveforms for blocking neural conduction. The systems and methods of neuromodulation disclosed herein facilitate the treatment of various diseases associated with pathological neural activity.

Embodiments of the present disclosure address the need for efficient and effective neural block by developing a model-based global optimization algorithm (e.g., particle swarm optimization (PSO) algorithm) to design an optimized waveform for neural block. This approach enables the systematic exploration of the full range of parameters for neural block, including waveform shape, frequency, and amplitude. In accordance with these embodiments, charge-balanced waveforms were designed to achieve neural block with minimum energy. The algorithm was validated by reproducing a minimum-energy waveform to elicit an action potential, and by performing sensitivity analyses on the algorithm's parameters to ensure robustness of its performance.

Global optimization algorithms have been used to minimize energy consumption of conventional waveforms for eliciting neural activity (neural stimulation or activation). The present disclosure provides methods for optimizing waveform shape to achieve efficient nerve fiber conduction block using a cost function with weighted performance criteria. The individual weights of each different performance criterion may be adjusted differentially (including to zero) to determine an optimal waveform for a specific criterion or combination of criteria. There are multiple suitable optimization algorithms that may be used individually or in combination to determine the optimal waveform for neural conduction block given a set of performance criteria, including, for example, a PSO algorithm, although other optimization algorithms may be used, as well as other versions of a PSO algorithm.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Correlated to" as used herein refers to compared to.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (e.g., a monkey, such as a cynomolgus or rhesus monkey, chimpanzee, etc.) and a human). In some embodiments, the subject may be a human or a non-human. In one embodiment, the subject is a human. The subject or patient may be undergoing various forms of treatment.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a treatment to a subject that is not at the time of administration afflicted with the disease. "Preventing" also refers to preventing the recurrence of a disease or of one or more symptoms associated with such disease.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, neurobiology, microbiology, genetics, electrical stimulation, neural stimulation, neural modulation, and neural prosthesis described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Particle Swarm Optimization Algorithm

Embodiments of the present disclosure include particle swarm optimization (PSO) algorithms used to determine an optimized waveform shape for neural conduction block. PSO is an iterative algorithm which seeks optimal solutions by applying heuristic updates to candidate solutions according to the current and previous best solutions within the swarm (collection of particles). Unlike genetic algorithms (GAs), all particles (analogous to genes of an individual in a GA) change state on every generation.

Table 1 below presents definitions of key terms used in the PSO, and the algorithm is diagrammed in FIG. 1.

TABLE 1

Definition of terms used in the particle swarm optimization (PSO) algorithm.

| Term | Definition | Conventional usage | Neural block usage |
| --- | --- | --- | --- |
| Particle | Candidate solution. | Ex.: Dot in 2D space. | Candidate waveform. Neural block threshold (minimum scaling of the waveform's amplitude to achieve block) is determined for each waveform. |
| Swarm | Collection of particles. | Ex.: N dots in 2D space of current generation. | Ex.: N waveforms of current generation. |
| Particle dimensions | Each particle has one or more dimensions, where each variable in the problem is represented by a dimension. | Ex.: x, y coordinate values. | The number of dimensions in each waveform is equal to the number of time points defining one period. |

TABLE 1-continued

Definition of terms used in the particle swarm optimization (PSO) algorithm.

| Term | Definition | Conventional usage | Neural block usage |
| --- | --- | --- | --- |
| Particle location | Each dimension of each particle has a variable value, termed "location". Each particle stores its best-achieved location. | Ex.: Values of x and y coordinates for a given particle. | Current amplitude of each time point of each waveform. |
| Particle velocity | How the location of the particle will be updated for the next generation. | Weighted difference between two particle locations or location vectors. | Weighted difference between two particle locations. |
| Cost | Function to be minimized. | Cost for each particle. | Waveform energy at block threshold. |

The swarm is a collection of waveforms that are intelligently updated based on a cost function and an updater function until termination criteria are met. Each waveform (particle) in the swarm consists of a sequence of time points (dimensions) (FIG. 1C). For example, designing a waveform with a period of 0.1 ms and a time step of 0.001 ms can result in 100 time points per waveform. The location of each time point was equal to the normalized current amplitude of the waveform at that time point. Block thresholds for each waveform were determined in the current swarm generation. The current amplitude for each time point in each waveform was then updated from one generation of the swarm to the next based on its own history and based on the current amplitudes at the same time point in other waveforms. This swarm evaluation and updating was repeated until the termination criteria were attained (FIG. 1A).

In some embodiments, using PSO to optimize waveforms for neural block involves randomly generating an initial group (swarm) of waveforms ("Generation 1"), and determining the block threshold for each waveform. Between generations, the fitness of each waveform (particle) can be assessed and the particle velocities updated to swarm towards the particle's new target, thereby defining a new generation of waveforms. While particles are typically updated by two of the fittest solutions, this updating depends on how the particles communicate, known as swarm connectivity or topology. Like similar evolutionary algorithms, the process of updating and evaluating the particles continues for a fixed number of generations or until some termination criterion is reached.

3. Evaluating Waveforms

Embodiments of the present disclosure include methods of evaluating different waveforms to determine their ability to achieve block of neural activity and/or the threshold intensity (current, frequency, voltage, power and/or energy) to achieve block and/or their net charge over one period and/or the resulting neural onset response, for different nerve fiber types and/or locations. There are different ways to evaluate the waveforms, including but not limited to the following approaches. If assuming quasi-static conditions with linear, non-dispersive tissue/material properties, the spatial distribution of potentials can be decoupled from their temporal shape (the waveform). In some embodiments, the spatial distribution of potentials can be obtained from analytical (e.g., point current source in a homogeneous infinite medium) or numerical (e.g., three-dimensional finite element model of a nerve and electrode) estimates for certain electrode design and tissue properties. The candidate waveforms can then be used to scale the extracellular potentials which are applied to a model neuron, and block is evaluated. Alternatively, the waveforms may be evaluated in a non-linear spatio-temporal model. Block may be evaluated by applying an intracellular current to evoke an action potential (or train of APs) proximally (intrinsic activity) and recording the transmembrane potential distally to verify whether the intrinsic neural activity was blocked.

To assess a waveform's performance or fitness (the reciprocal or the negative of cost), the waveform's block threshold can be determined using a non-linear cable model of a neuron. In some embodiments, a binary search algorithm determines the minimum stimulation amplitude required to achieve action potential conduction block (block threshold). Total waveform energy (in $J/\Omega$) can be calculated by multiplying the waveform shape by the block threshold value, squaring the scaled waveform, summing across time points, and multiplying by the time step. If block is not achieved at the upper bound of the binary search, a cost penalty with a value substantially higher than any expected waveform energy at threshold (e.g., 1 $\mu J/\Omega$) can be assessed, thereby preventing the waveform from influencing the search for other waveforms. The waveform energy can be computed over one period, over a set length of time, or over the entire simulation duration.

In some embodiments, a requirement for charge balance can be imposed by translating every new waveform vertically as needed, using the same additive translation factor for every time point in a given waveform. Alternatively, a tolerance for charge imbalance can be defined and included as a weighted term in the fitness function. Indeed, while the cost function can account for energy and block efficacy, it could also have weighted terms to include charge imbalance, the size/duration of the onset response, and the type, diameter, and location of the fiber(s) targeted for block.

In some embodiments, waveforms can be defined and evaluated by optimizing one period of the KHF waveform. For example, the PSO may be run to define a waveform over 0.1 ms which is then repeated through concatenation to create a signal that is 100 ms in duration and has a repetition frequency of 10 kHz. For each kilohertz frequency, 40 time points per waveform were used (per period of the signal) resulting in time steps of 5, 2.5, and 1.25 $\mu s$ for the 5, 10, and 20 kHz waveforms, respectively. Block threshold was determined for each waveform (e.g., using NEURON v7.4) using a 35-node (51 mm), 16 $\mu m$ myelinated axon with passive (linear) end-nodes. The McIntyre-Richardson-Grill (MRG) model axon was used, given its mammalian ultrastructure and ion channels, as well as its extensive validation for many output measures, including KHF block. Extracellular potentials were delivered from a point source in a homogeneous, isotropic, infinite medium (300 Ω-cm), 1 mm away from the middle node of Ranvier. Block threshold was found using a binary search algorithm, exiting when the lower and upper bounds were within 1% of each other. The initial lower and upper bounds were zero and −2 mA, respectively. The upper bound on the binary search was intelligently adjusted as the PSO progressed: after the first generation, the upper bound was set to 110% of the previous blocking threshold, since waveform shape only changes incrementally between generations. Further, if a specific waveform could achieve block with a higher amplitude than the upper bound, its energy would be too high to result in identification as a neighborhood or global leader, in which case knowledge of its energy at block threshold is unnecessary. If a waveform does not achieve block within the tested amplitude bounds, the upper bound was reset to −2 mA in the following generation. Each simulation was initialized with 10 ms timesteps from t=−200 ms to t=0 ms to ensure initial steady-state. A 27 ms simulation was then conducted, starting the PSO waveform at 0 ms, using backward Euler integration. Suprathreshold intracellular test pulses were delivered at 100 Hz, applied 6 mm from the proximal end, starting at 15 ms. Block was identified as having zero action potentials at the first 5 nodes from the distal end, where an action potential was defined as a rising edge passing −20 mV.

For each waveform, energy (in J/Ω) for one period was calculated using the below equation:

$$E = dt * I_{th}^2 * \sum_{i=0}^{T/dt} p_i^2$$

where dt is the time step, $I_{th}$ is the block threshold, T is the duration of the waveform in the PSO (i.e. the period of the waveform used in NEURON), i designates the index of a particular time point, and p is the location of each time point. Note that $I_{th}*p_i$ results in a current amplitude. If block was not achieved at the upper bound of the binary search, a cost penalty with a value substantially higher than any expected waveform energy at threshold (1 μJ/Ω) was assigned as the energy value, thereby preventing the waveform from influencing the search for other waveforms.

Before comparing the energy of different waveforms for a given generation of the swarm, a possibility that the swarm may contain phase-shifted copies of same waveform was considered, impeding convergence and local exploration. To identify and address this issue, each waveform was shifted periodically (every 10 generations with default parameters) to maximize the cross-correlation with the global leader (see below; computed using MATLAB's xcorr function). In some cases, each waveform was shifted using the lag at which the cross-correlation was maximized. This can shift all particles in the waveform to new time points to allow more relevant updating while maintaining the same periodic waveform.

4. Pso Topology

One embodiment of the particle swarm optimization (PSO) algorithm is diagrammed in FIG. 1, with an overview of the workflow in FIG. 1A, and the algorithm is further described in the text below.

PSO algorithms can use various particle communication networks (topologies) that dictate how the particle velocities, and by extension, their locations, can be updated between generations. Established PSO topologies include the fully connected network, in which particles draw influence from all particles' best locations, and the ring network, in which particles draw influence from the fittest particle's personal best location. Particles (or waveforms) may also be grouped and then updated according to group and/or global leaders. One such neighborhood topology is termed the "winner-takes-all" particle swarm, which consists of dynamic, hierarchal connectivity between particles, such that each particle is classified as either a neighborhood agent, a neighborhood leader, or the global leader (FIG. 1B), limiting the speed of influence to avoid premature convergence on a local minimum and promoting global exploration of the parameter space. This topology is especially well-suited for waveform optimization given its success in solving high-dimensional problems and reaching termination criteria in fewer generations than other PSO topologies.

Generally, each waveform in a swarm consists of a sequence of time points, where each time point is a dimension of the particle (FIG. 1C). For example, designing a waveform that is 0.1 ms in duration with a time step of 0.001 ms resulted in 100 particles (time points) per waveform. The number of particles at a given time step can be equal to the number of waveforms in the swarm; for example, with 100 time points per waveform and 50 waveforms in the swarm, there are 50 particles at t=0.008 ms. Each particle location can be equal to the normalized current amplitude of the waveform at that time point. Each particle location remained at the same time step in the same waveform across all generations, and it simply fluctuates up and down according to its updater function, except if the waveform was phase-shifted to maximize the cross-correlation with the global leader. Each time step in each waveform updated its velocity based only on its own history and on the amplitudes of the same time step in other waveforms, but cost was evaluated for the entire waveform (particle). When assessing cost, each waveform (consisting of a static combination of constituent particle dimensions) was evaluated to determine the minimum required amplitude (scaling factor) to achieve neural block (block threshold). This block threshold was applied to all particle dimensions of that particular waveform. Therefore, particles were effectively updated to swarm toward locations corresponding to the locations of particles in the fittest waveforms.

In one embodiment of the "winner-takes-all" PSO topology, a swarm was defined with 50 waveforms per generation, grouped into 5 neighborhoods with 10 waveforms each. The waveforms stayed in the same neighborhoods throughout the algorithm. The current amplitude for each time point in each waveform was updated between generations based on its own history and based on two influencing waveforms (FIG. 1B; Table 2).

TABLE 2

Summary of influencing waveforms used in an implementation of the winner-takes-all PSO topology.

| Waveform | Influencer 1 (I1) | Influencer 2 (I2) |
|---|---|---|
| Global leader (GL) | Itself (GL) | Fittest NL |
| Neighborhood leader (NL) | GL | Fittest NL other than itself |
| Neighborhood agent | NL | Fittest waveform in the neighborhood that's not NL or GL |

For each generation, the fittest waveform in the swarm was the global leader. The fittest waveform in each neighborhood was selected as a neighborhood leader, unless that waveform was the global leader, in which case the second-fittest waveform was neighborhood leader. The remaining waveforms in each neighborhood were referred to as neighborhood agents. The global leader was influenced by itself and by the fittest neighborhood leader. Each neighborhood leader was influenced by the global leader and by the fittest neighborhood leader other than itself. Each neighborhood agent was influenced by the neighborhood leader and by the best performing waveform within its neighborhood that was not a global or neighborhood leader. Each neighborhood agent was influenced by the neighborhood leader and by the best performing waveform within its neighborhood that was not the global leader or a neighborhood leader or itself. For each influencing waveform, the lowest-energy generation (not necessarily the current generation) was used in the calculation of the particles' velocity.

The PSO algorithm according to one embodiment of the present disclosure is detailed in FIG. 1D. An initial swarm of waveforms was randomly generated by drawing amplitudes from a uniform random distribution. Each waveform was vertically shifted to achieve zero net charge and each waveform was scaled to have an absolute peak of 1. The block threshold for each waveform was determined and the current generation's global and neighborhood leaders were identified (see above). To generate subsequent generations of waveforms, the velocity of the amplitude was calculated for each waveform with the equation below:

$$\overrightarrow{v_{j,k+1}} = w_{1,k} * [\overrightarrow{v_{j,k}} + U(-0.2, 0.2)] +$$
$$w_2 * [(\overrightarrow{p_{I1,k}} - \overrightarrow{p_{j,k}}) * U(0, 1) + (\overrightarrow{p_{I2,k}} - \overrightarrow{p_{j,k}}) * U(0, 1)]$$

where:

Each position vector ($\vec{p}$) and velocity vector ($\vec{v}$) has one element for each time point; j is the waveform number; I1 and I2 are the particle's first and second influencers respectively (Error! Reference source not found.); k is the generation number; $\vec{p}$ is the particle location (i.e., normalized current amplitude); $\vec{v}$ is the particle velocity; $w_1$ is the inertial weighting coefficient; $w_2=1.5$; and $U(a,b)$ indicates a scalar drawn from a random uniform distribution from a to b (both bounds included).

The first term (inertial/exploration term) may prevent premature convergence and promote global exploration, although in the default parameters, $w_1=0$. The inertial term contains information about a particles' past velocities, as well as a zero-mean, uniform random term, allowing further exploration in case the particle velocity v approaches zero prematurely. The weighting of this inertial term, $w_1$, a value greater than or equal to zero, may help to ensure that the particle velocity would not converge prematurely or diverge, which would result in suboptimal solutions. The value of $w_1$ was specific for each neighborhood for each generation according to the average particle velocity, a metric directly related to the particles' average distance from the best solutions; the neighborhood-specific $w_1$ values provided freedom for each neighborhood to explore their space as long as needed and to converge on their optimal solution at an appropriate time for their neighborhood. $w_1$ was initialized to $v_{init}=v_{ideal,1}$ and updated to produce a linearly decreasing average neighborhood velocity across generations, resulting in monotonically decreasing fitness values. The $v_{ideal,k}$ was then decreased with each generation such that it reached zero at a set number of exploration generations (see PSO Termination Criteria), encouraging convergence. For each neighborhood at each generation k, if the neighborhood's average particle velocity ($v_{avg,k}$) was more than 1% away from $v_{ideal,k}$, then $w_{1,k}$ was adjusted from its previous estimate (see equation below).

if $(v_{avg,k} > 1.01 * v_{ideal,k}) \| (v_{avg,k} < 0.99 * v_{ideal,k})$ $w_{1,k} = \left(\frac{v_{ideal,k}}{v_{avg,k}}\right) * w_{1,k-1}$ else $w_{1,k} = w_{1,k-1}$ Thus, each neighborhood of the swarm was updated independently, each with its own inertial weighting coefficient $w_1$. This design choice prevented convergence in some neighborhoods from causing $w_1$ to increase across all neighborhoods, which in turn would cause an increase in average velocity and potential divergence in neighborhoods that have not yet converged.

The second term in the velocity equation was the exploitation term. In this term, the particle velocity was updated by the difference between the particle's current location and the best locations of its two influencing particles. These two difference terms were each multiplied by a value drawn from U(0,1), varying the influence of the updating particles at every generation and sometimes allowing one updater to dominate over the other. The coefficient of the second term, $w_2$, was static. Its value of 1.5, now commonly used in particle swarm implementations, was derived from mathematical analysis. In conjunction with the random weighting of influencer particles, this choice for $w_2$ enabled the exploration of potential solutions by causing particles to either overshoot or undershoot their target location, oscillating about the target solution to ensure sufficient global search.

Finally, the particle velocities were used to compute the new particle locations (see equation below).

$p_{i,j,k+1} = p_{i,j,k} + v_{i,j,k+1}$

As with the initial waveforms, each new waveform was vertically shifted to impose zero net charge and scaled to have an absolute peak of 1.

The iteration of generating a swarm of candidate waveforms and evaluating their block thresholds was repeated for at least 50 generations with default parameters (see Table 3). Two termination criteria were then verified: convergence of swarm and stability of minimum energy. The convergence of the swarm involved calculating the percent difference in energy between the waveform with the lowest best-ever energy and the waveform with the highest best ever energy; it was then compared to the swarm convergence threshold (1% default value). The stability of the swarm minimum energy involved calculating the percent change in the best-ever energy of the global leader over 25 generations ("minimum number of stability generations"); it was then compared to the stability threshold (1% default value). If either termination criterion was met after 50 generations ("minimum number of generations"), then the algorithm was terminated. Otherwise, another generation was added and the 25-generation stability window was slid forward, until the convergence criterion or stability criterion was met.

5. Methods and Systems

In accordance with the above description, embodiments of the present disclosure include methods of identifying an optimized waveform shape for blocking neural conduction. In some embodiments, the method includes generating a plurality of waveforms using a global optimization algorithm based on predetermined performance criteria, evaluating the plurality of waveforms for neuronal conduction block using a computational model of extracellular neuronal stimulation, and identifying at least one candidate waveform having an optimized shape capable of blocking neural conduction.

In some embodiments, generating a plurality of waveforms is performed using a global optimization algorithm. The global optimization algorithm can include, but is not limited to, a genetic algorithm, a particle swarm algorithm, a simulated annealing algorithm, an ant colony algorithm, an estimation of distribution algorithm, and any combinations and derivations thereof. In some embodiments, the global optimization algorithm is a particle swarm optimization (PSO) algorithm, and when generating the plurality of waveforms, the minimum swarm energy of the PSO algorithm varies less than about 0.1% to about 10.0% over from about 10 generations to about 100 generations after completing a minimum number of generations, or the minimum and maximum waveform energies in the swarm at a given generation were less than 10% apart after completing a minimum number of generations, or any combinations and derivatives thereof.

In some embodiments, generating a plurality of waveforms is performed using a global optimization algorithm that is based on predetermined performance criteria. In accordance with these embodiments, the predetermined performance criteria can be incorporated into a cost function used to evaluate the fitness of the plurality of waveforms. As described herein, the cost function for a simulation can be the waveform energy to achieve block (improved block efficiency). Sensitivity analysis can be conducted where the cost function also includes charge-balance, rather than enforcing zero net charge at all times. This approach may be broadened to include a customizable, multi-objective cost function. The cost function can also include additional weighted performance criteria, such as, but not limited to, minimizing energy required for conduction block, minimizing power required for conduction block, minimizing charge imbalance in the optimized waveform, minimizing onset response produced when the optimized waveform is turned on, maximizing degree of conduction block, minimizing voltage or current required for conduction block with the optimized waveform, maximizing therapeutic benefit produced by application of the optimized waveform, minimizing adverse effect produced by application of the optimized waveforms, maximizing selectivity of block between nerve fiber types blocked by application of the optimized waveform, maximizing selectivity of block between nerve fiber diameters blocked by application of the optimized waveform, maximizing selectivity between nerve fiber locations blocked by application of the optimized waveform, and any combinations and derivatives thereof. The individual weights of each different performance criterion may be adjusted differentially (including to zero) to determine an optimal waveform for a specific criterion or combination of criteria. The cost function may also include penalty terms, including but not limited to failure to achieve conduction block, lack of charge-balance, and block or stimulation of off-target fibers, and the individual penalty terms may also be adjusted differentially (including to zero) using individual weights.

In some embodiments, the predetermined performance criteria comprise minimizing the energy required for conduction block. In some embodiments, the predetermined performance criteria comprise minimizing the onset response produced when the optimized waveform is turned on and maximizing selectivity of block between nerve fiber types blocked by application of the optimized waveform, maximizing selectivity between nerve fiber diameters blocked by application of the optimized waveform, and/or maximizing selectivity of block between nerve fiber locations blocked by application of the optimized waveform. And in some embodiments, the predetermined performance criteria comprise maximizing the degree of neural conduction block, minimizing charge imbalance in the optimized waveform, and/or minimizing power required for conduction block.

In accordance with these embodiments, the plurality of waveforms for neuronal conduction block can be evaluated using a computational model of extracellular neuronal stimulation, and in some embodiments, the computational model of extracellular neuronal stimulation can be coupled to the global optimization algorithm based on the predetermined performance criteria. Computational models, such as those that represent the anatomical, morphological, and biophysical properties of the nerve fibers of interest, can enable efficient exploration and rigorous optimization of application-specific parameters, as described further herein. In some embodiments, the extracellular potentials are estimated using analytical methods (e.g., point current source in a homogeneous infinite medium). In some embodiments, the extracellular potentials are estimated using numerical methods (e.g., three-dimensional finite element model of a nerve and electrode). In some embodiments, the computational model comprises a model of an A-type myelinated axon. In some embodiments, the computational model comprises a model of a B-type myelinated axon. In some embodiments, the computational model comprises a model of a C-type unmyelinated axon. In some embodiments, the computational model comprises a model of a presynaptic terminating axon. In some embodiments, the computational model comprises a model of a neuron comprising representations of the dendrites, cell body, and axon, or components thereof. In some embodiments, the computation model comprises a model of an afferent neuron or an efferent neuron. Additionally, as would be recognized by one of ordinary skill in the art based on the present disclosure, other computational models can also be used in conjunction with the methods and systems designed herein.

In accordance with these embodiments, the method also includes identifying at least one candidate waveform having an optimized shape capable of blocking neural conduction. In some embodiments, the candidate waveform is monophasic. In other embodiments, the candidate waveform is multiphasic, including a waveform that is charge-balanced and/or biphasic.

In some embodiments, the candidate waveform can block neural conduction at a waveform repetition frequency from about 1 to about 100 kHz. In some embodiments, the candidate waveform can block neural conduction at a waveform repetition frequency from about 1 to about 80 kHz. In some embodiments, the candidate waveform can block neural conduction at a waveform repetition frequency from about 1 to about 60 kHz. In some embodiments, the candidate waveform can block neural conduction at a waveform repetition frequency from about 1 to about 40 kHz. In some embodiments, the candidate waveform can block neural conduction at a waveform repetition frequency from about 1 to about 20 kHz. In some embodiments, the candidate waveform can block neural conduction at a waveform repetition frequency from about 5 to about 20 kHz. In some embodiments, the candidate waveform can block neural conduction at a waveform repetition frequency from about 5 to about 15 kHz. In some embodiments, the candidate waveform can block neural conduction at a waveform repetition frequency from about 5 to about 10 kHz. In some embodiments, the candidate waveform can block neural conduction at a waveform repetition frequency from about 10 to about 20 kHz.

In some embodiments, the shape of the optimized waveform minimizing the energy required for conduction block comprises a higher, narrower anodic phase and a shallower, broader cathodic phase. In some embodiments, the shape of the optimized waveform can be described as or based on a sum of sinusoidal functions, a sum of Gaussian functions, or a sum or ratio of any other functional forms, as would be recognized by one of ordinary skill in the art based on the present disclosure.

In some embodiments, the minimum energy of the optimized waveform is from about 5% to about 80% of the energy required for conduction block with a waveform generated without using the global optimization algorithm, such as a sinusoid, a symmetric charge-balanced rectangular waveform with 100% duty cycle, or a symmetric charge-balanced rectangular waveform with 25 µs per phase. In some embodiments, the minimum energy of the optimized waveform is from about 5% to about 10% of the energy required for conduction block with a waveform generated without using the global optimization algorithm. In some embodiments, the minimum energy of the optimized waveform is from about 5% to about 20% of the energy required for conduction block with a waveform generated without using the global optimization algorithm. In some embodiments, the minimum energy of the optimized waveform is from about 5% to about 30% of the energy required for conduction block with a waveform generated without using the global optimization algorithm. In some embodiments, the minimum energy of the optimized waveform is from about 5% to about 40% of the energy required for conduction block with a waveform generated without using the global optimization algorithm. In some embodiments, the minimum energy of the optimized waveform is from about 5% to about 50% of the energy required for conduction block with a waveform generated without using the global optimization algorithm. In some embodiments, the minimum energy of the optimized waveform is from about 5% to about 60% of the energy required for conduction block with a waveform generated without using the global optimization algorithm. In some embodiments, the minimum energy of the optimized waveform is from about 5% to about 70% of the energy required for conduction block with a waveform generated without using the global optimization algorithm. In some embodiments, the minimum energy of the optimized waveform is from about 10% to about 20% of the energy required for conduction block with a waveform generated without using the global optimization algorithm. In some embodiments, the minimum energy of the optimized waveform is from about 20% to about 30% of the energy required for conduction block with a waveform generated without using the global optimization algorithm. In some embodiments, the minimum energy of the optimized waveform is from about 30% to about 40% of the energy required for conduction block with a waveform generated without using the global optimization algorithm. In some embodiments, the minimum energy of the optimized waveform is from about 40% to about 50% of the energy required for conduction block with a waveform generated without using the global optimization algorithm. In some embodiments, the minimum energy of the optimized waveform is from about 50% to about 60% of the energy required for conduction block with a waveform generated without using the global optimization algorithm. In some embodiments, the minimum energy of the optimized waveform is from about 60% to about 70% of the energy required for conduction block with a waveform generated without using the global optimization algorithm. In some embodiments, the minimum energy of the optimized waveform is from about 7% to about 80% of the energy required for conduction block with a waveform generated without using the global optimization algorithm.

In some embodiments, the minimum energy of the candidate waveform is from about 9.0 pJ/Ω to about 20.0 pJ/Ω for one period at about 5 kHz to about 20 kHz. In some embodiments, the minimum energy of the candidate waveform is from about 10.0 pJ/Ω to about 20.0 pJ/Ω for one period at about 5 kHz to about 20 kHz. In some embodiments, the minimum energy of the candidate waveform is from about 12.0 pJ/Ω to about 20.0 pJ/Ω for one period at about 5 kHz to about 20 kHz. In some embodiments, the minimum energy of the candidate waveform is from about 14.0 pJ/Ω to about 20.0 pJ/Ω for one period at about 5 kHz to about 20 kHz. In some embodiments, the minimum energy of the candidate waveform is from about 16.0 pJ/Ω to about 20.0 pJ/Ω for one period at about 5 kHz to about 20 kHz. In some embodiments, the minimum energy of the candidate waveform is from about 18.0 pJ/Ω to about 20.0 pJ/Ω for one period at about 5 kHz to about 20 kHz.

Embodiments of the present disclosure also include a system for blocking neural conduction. In accordance with these embodiments, the system includes an electrode sized and configured for implantation in proximity to neural tissue, and a pulse generator coupled to the electrode, the pulse generator including a power source comprising a battery and a microprocessor coupled to the battery, wherein the pulse generator is capable of applying to the electrode a stimulation waveform having an optimized shape capable of blocking neural conduction.

In some embodiments of the system, the stimulation waveform shape is optimized to meet performance criteria comprising at least one of: minimizing energy required for conduction block, minimizing power required for conduction block, minimizing charge imbalance in the optimzed waveform, minimizing onset response produced when the optimized waveform is turned on, maximizing degree of conduction block, minimizing voltage or current required for conduction block with the optimized waveform, maximizing therapeutic benefit produced by application of the optimized waveform, minimizing adverse effect produced by application of the optimized waveforms, maximizing selectivity between nerve fiber types blocked by application of the optimized waveform, maximizing selectivity between nerve fiber diameters blocked by application of the optimized waveform, maximizing selectivity between nerve fiber locations blocked by application of the optimized waveform, and any combinations and derivatives thereof.

In some embodiments of the system, the stimulation waveform comprises an optimized shape capable of blocking neural conduction with minimum energy. In some embodiments of the system, the stimulation waveform blocks neural conduction at a waveform repetition frequency from about 1 to about 100 kHz. In some embodiments, the candidate waveform can block neural conduction at a waveform repetition frequency from about 1 to about 80 kHz. In some embodiments, the candidate waveform can block neural conduction at a waveform repetition frequency from about 1 to about 60 kHz. In some embodiments, the candidate waveform can block neural conduction at a waveform repetition frequency from about 1 to about 40 kHz. In some embodiments, the candidate waveform can block neural conduction at a waveform repetition frequency from about 1 to about 20 kHz. In some embodiments, the candidate waveform can block neural conduction at a waveform repetition frequency from about 5 to about 20 kHz. In some embodiments, the candidate waveform can block neural conduction at a waveform repetition frequency from about 5 to about 15 kHz. In some embodiments, the candidate waveform can block neural conduction at a waveform repetition frequency from about 5 to about 10 kHz. In some embodiments, the candidate waveform can block neural conduction at a waveform repetition frequency from about 10 to about 20 kHz.

In some embodiments of the system, the energy-optimized shape of the candidate waveform comprises a higher, narrower anodic phase and a shallower, broader cathodic phase. In some embodiments, the shape of the optimized waveform can be described as or based on a sum of sinusoidal functions, a sum of Gaussian functions, or a sum of any other functional forms, as would be recognized by one of ordinary skill in the art based on the present disclosure.

In some embodiments of the system, the minimum energy of the candidate waveform is from about 9.0 pJ/Ω to about 20.0 pJ/Ω for one period at about 5 kHz to about 20 kHz. In some embodiments, the minimum energy of the candidate waveform is from about 10.0 pJ/Ω to about 20.0 pJ/Ω for one period at about 5 kHz to about 20 kHz. In some embodiments, the minimum energy of the candidate waveform is from about 12.0 pJ/Ω to about 20.0 pJ/Ω for one period at about 5 kHz to about 20 kHz. In some embodiments, the minimum energy of the candidate waveform is from about 14.0 pJ/Ω to about 20.0 pJ/Ω for one period at about 5 kHz to about 20 kHz. In some embodiments, the minimum energy of the candidate waveform is from about 16.0 pJ/Ω to about 20.0 pJ/Ω for one period at about 5 kHz to about 20 kHz. In some embodiments, the minimum energy of the candidate waveform is from about 18.0 pJ/Ω to about 20.0 pJ/Ω for one period at about 5 kHz to about 20 kHz.

Embodiments of the present disclosure also include a method for blocking neural conduction using embodiments of the systems and methods as described above. In accordance with these embodiments, the method includes programming the pulse generator to output the stimulation waveform (e.g., on a graphical user interface (GUI)), the stimulation waveform representing a waveform having an optimized shape capable of blocking neural conduction, and setting amplitude of the stimulation waveform, wherein the stimulation waveform blocks neural conduction when delivered by the pulse generator.

In some embodiments, the stimulation waveform shape is optimized to meet performance criteria comprising at least one of: minimizing energy required for conduction block, minimizing power required for conduction block, minimizing charge imbalance in the optimized waveform, minimizing onset response produced when the optimized waveform is turned on, maximizing degree of conduction block, minimizing voltage or current required for conduction block with the optimized waveform, maximizing therapeutic benefit produced by application of the optimized waveform, minimizing adverse effect produced by application of the optimized waveforms, maximizing selectivity of block between nerve fiber types blocked by application of the optimized waveform, maximizing selectivity of block between nerve fiber diameters blocked by application of the optimized waveform, maximizing selectivity of block between nerve fiber locations blocked by application of the optimized waveform, and any combinations and derivatives thereof.

In some embodiments, the stimulation waveform comprises an optimized shape capable of blocking neural conduction with minimum energy. In some embodiments, the waveform blocks neural conduction at a waveform repetition frequency from about 1 to about 100 kHz. In some embodiments, the optimized shape of the candidate waveform to block with minimum energy comprises a higher, narrower anodic phase and a shallower, broader cathodic phase. In some embodiments, the shape of the optimized waveform can be described as or based on a sum of sinusoidal functions, a sum of Gaussian functions, or a sum of any other functional forms, as would be recognized by one of ordinary skill in the art based on the present disclosure.

In accordance with embodiments of the system for blocking neural conduction as described above, the electrode or lead can be placed in a desired position in contact with nervous system tissue of a subject receiving neural block conduction treatment. In one embodiment, the electrode can be implanted in a region of the brain, such as the thalamus, subthalamus, or globus pallidus for the purpose of deep brain stimulation. However, as would be recognized by one of ordinary skill in the art based on the present disclosure, the electrode can be implanted in, on, or near the spinal cord; or in, on, or near a peripheral nerve (sensory or motor or mixed; somatic or autonomic); or in, or, or near a neural plexus; or in, on, or near any subcutaneous tissue such as muscle tissue (including cardiac tissue) or adipose tissue or other organ tissue for the purpose of stimulation to achieve a therapeutic purpose. In addition, the electrode may be utilized for transcutaneous stimulation where electrodes are placed, not subcutaneous, but on an outer skin surface.

The electrode can be one or more electrodes configured as part of the distal end of a lead or be one or more electrodes configured as part of a leadless system to apply electrical pulses to the targeted tissue region. Electrical pulses can be supplied by a pulse generator coupled to the electrode/lead. In one embodiment, the pulse generator can be implanted in a suitable location remote from the electrode/lead (e.g., in the shoulder region); however, that the pulse generator could be placed in other regions of the body or externally to the body.

When implanted, at least a portion of the case or housing of the pulse generator can serve as a reference or return electrode. Alternatively, the lead can include a reference or return electrode (comprising a multipolar (such as bipolar) arrangement), or a separate reference or return electrode can be implanted or attached elsewhere on the body (comprising a monopolar arrangement).

The pulse generator can include stimulation generation circuitry, which can include an on-board, programmable microprocessor, which has access to and/or carries embedded code. The code expresses pre-programmed rules or algorithms under which desired electrical stimulation is generated, having desirable electrical stimulation parameters that may also be calculated by the microprocessor, and distributed to the electrode(s) on the lead. According to these programmed rules, the pulse generator directs the stimulation through the lead to the electrode(s), which serve to selectively stimulate the targeted tissue region. The code may be programmed, altered or selected by a clinician to achieve the particular physiologic response desired. Additionally or alternatively to the microprocessor, stimulation generation circuitry may include discrete electrical components operative to generate electrical stimulation having desirable stimulation parameters. As described herein, the stimulation parameters can be input to generate an optimized waveform shape, which can include a pulse amplitude; a pulse width (PW) or duration; a frequency of stimulation pulses applied over time; and a shape or waveform of the stimulation pulses. One or more of the parameters may be prescribed or predetermined as associated with a particular treatment regime or indication (e.g., in accordance performance criteria). In some embodiments, the pulse generator can be programed to output a stimulation waveform (e.g., on a graphical user interface (GUI)), and the stimulation waveform can represent a waveform having an optimized shape capable of blocking neural conduction, as described further herein. In some embodiments, programming the pulse generator includes setting the amplitude of the stimulation waveform, such that the stimulation waveform blocks neural conduction when delivered by the pulse generator.

In one embodiment, an on-board primary cell battery supplies power to the microprocessor and related circuitry. Currently, batteries must be replaced every 1 to 9 years, depending on the stimulation parameters needed to treat a disorder. When the battery life ends, the replacement of batteries requires another invasive surgical procedure to gain access to the implanted pulse generator. As described herein, the systems of the present disclosure make possible, among its several benefits, an increase in battery life.

In one embodiment, an on-board rechargeable battery supplies power to the microprocessor and related circuitry. Currently, batteries must be recharged every 1 to 30 days, depending on the stimulation parameters needed to treat a disorder. This requires the patient to remember to recharge frequently and to take the time to recharge. Additionally, the patient must frequently interact with their therapy, reminding them of their condition. As described herein, the systems of the present disclosure make possible, among its several benefits, an increase in battery life.

As will be described in greater detail later, the stimulation parameters, which may be prescribed, used by the pulse generator differ from conventional stimulation parameters, which may be prescribed, in that the waveform shape of the pulses has been optimized by use of an optimization algorithm, such as a global optimization algorithm. An example of a global optimization algorithm used to optimize an electrical stimulation waveform is a genetic algorithm (GA) or particle swarm algorithm used to optimize energy efficiency of a waveform for neural stimulation. Use of the waveform shapes optimized for energy-efficiency leads to a decrease in power consumption, thereby prolonging battery life, reducing battery size requirements, and/or reducing frequency of battery replenishment.

Although the following description is based largely on a particle swarm optimization algorithm, other optimization algorithms may be employed in a computational model of neural stimulation to optimize the stimulation based on a cost function, which can include a variety of factors, such as energy efficiency. Other optimization algorithms that may be used include, for example, simulated annealing, Monte-Carlo methods, other evolutionary algorithms (e.g. genetic algorithm), swarm algorithms (e.g. ant colony optimization, bees optimization), differential evolution, firefly algorithm, invasive weed optimization, harmony search algorithm, and/or intelligent water drops. Additionally, as would be recognized by one of ordinary skill in the art based on the present disclosure, other optimization methods and algorithms can also be used in conjunction with the methods and systems designed herein.

6. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Optimized Monophasic Waveforms Produces Excitation With Minimum Energy

Previous studies have designed optimized waveforms that minimize the energy required for nerve fiber activation using a genetic algorithm (GA). The PSO algorithm was implemented and evaluated to generate monophasic waveforms with minimized energy to excite a model axon (initiate an action potential) and compared these results to those using the GA. The normalized amplitudes of the excitation waveforms were constrained between 0 and −2, thus delivering cathodic current to cause membrane depolarization near the electrode, and the initial swarm velocity was set to 0.2 (units of normalized current). The waveform was optimized over 0.5 ms (dt=0.002 ms), resulting in 250 particles per waveform, and zero-padded the end of the waveform (3 ms total duration) to allow for detection of the propagating neural activity. Threshold excitation was determined for each waveform in NEURON v7.3 using a model of a 21-node, 11.5 μm myelinated axon, with extracellular potentials delivered via a point source in a homogeneous, isotropic, infinite medium (300 Ω-cm), 1 mm away from the middle node of Ranvier. The PSO was run with 50 waveforms per generation, grouped into 5 neighborhoods with 10 waveforms each.

In addition to using different optimization approaches (GA versus PSO), the algorithms also differed in their approaches for evaluating waveforms. Threshold for each waveform in the PSO was found, thereby allowing the PSO to focus on the waveform shape. Conversely, the previous GA study evaluated each waveform as is, applying a penalty if a waveform failed to elicit an action potential, thereby requiring the GA to account for waveform shape and amplitude.

The energy-optimized monophasic waveform of the previous GA study was reproduced using PSO (FIG. 2A). Specifically, a pulse energy (2.93 pJ/Ω) was achieved within 1% of the minimum energy within 350 generations, compared to over 4000 generations required by the previous GA study to identify the optimal solution (FIG. 2B).

Example 2

Optimized Biphasic Waveform Produces Excitation With Minimum Energy

The GA results were also used to optimize charge-balanced biphasic waveforms, where a rectangular anodic charge-balancing phase was added before or after the optimized cathodic waveform. The same approach and parameters described above for the monophasic waveform was used. Different combinations of cathodic pulse width (0.1 to 0.5 ms) and ratio of anodic to cathodic pulse width (1 to 10) were evaluated.

Figures 3A, 3B, 3C, 3D:
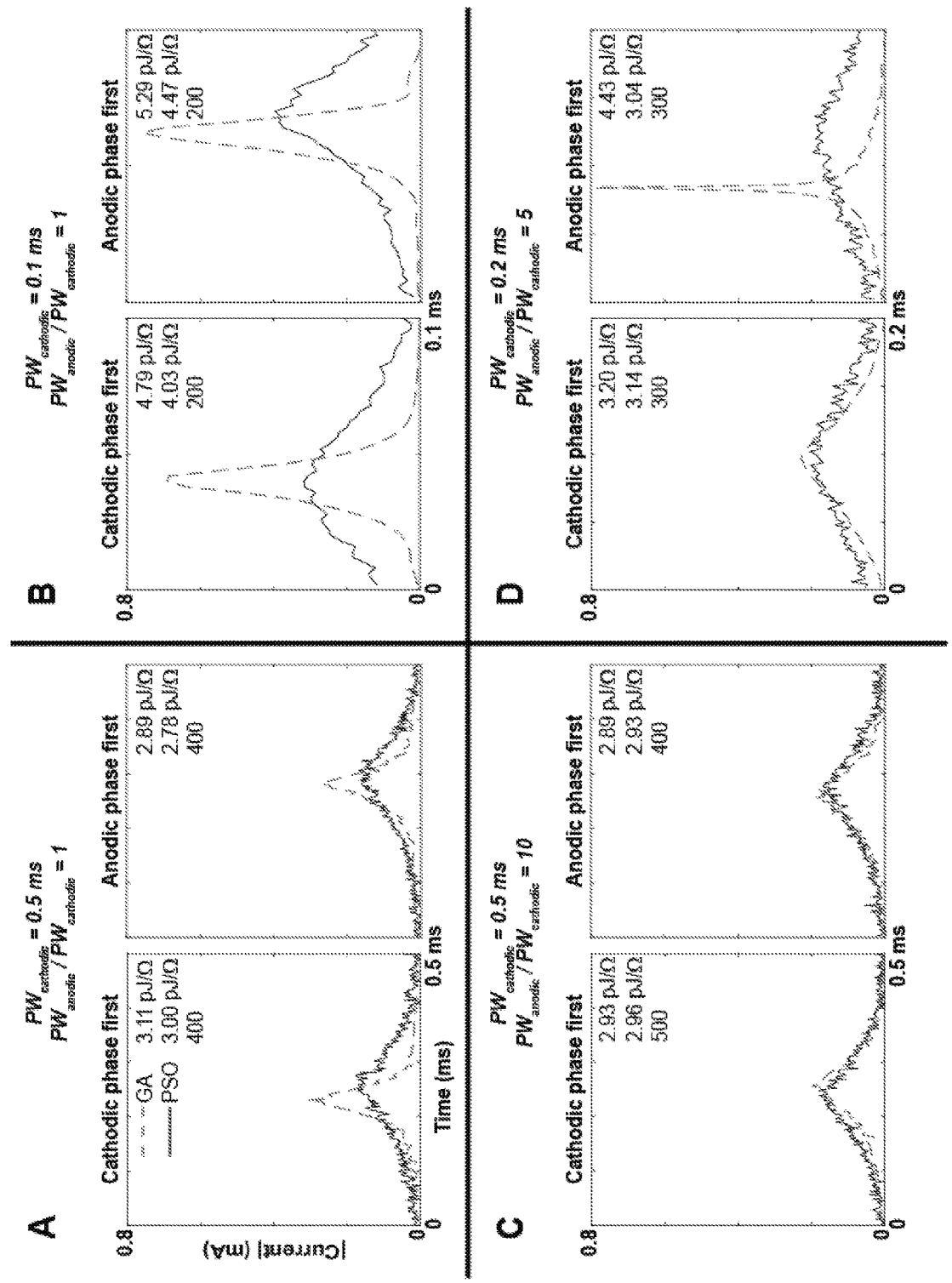
FIGS. 3A-3D include representative optimized charge-balanced (biphasic) waveforms for action potential initiation. Different cathodic pulse widths ($PW_{cathodic}$) and different values for the ratio of the anodic to cathodic pulse width ($PW_{anodic}/PW_{cathodic}$) were evaluated, as indicated in the title of each quadrant (FIGS. 3A-3D). The PSO algorithm was used to determine the shape of the cathodic phase, and a charge-balancing anodic phase was added afterwards ("Cathodic phase first;" left-hand panel in each quadrant) or before ("Anodic phase first;" right-hand panel in each quadrant). The cathodic phase waveforms are shown here using positive current for illustration. The waveforms from the GA study are shown as the red dashed lines, with the corresponding energy as the top value in each panel. The solid black lines are from the PSO algorithm, with the corresponding energy as the middle value in each panel. The energy values are only for the cathodic phase. The bottom value in each panel indicates the final generation for the PSO waveforms. The same time step was used for all pulse widths; therefore, the shorter pulse width (FIG. 3B) has fewer time points, causing the waveform to appear smoother.

The results are shown in FIGS. 3A-3D. As in the GA study, when the anodic charge-balancing phase preceded the cathodic pulse ("Anodic phase first" in FIG. 3), the peak of the cathodic pulse was shifted later in time as compared to the waveforms with an appended anodic phase ("Cathodic phase first"). However, lower-energy waveforms with broader profiles were found as compared to the GA study in certain cases (FIGS. 3A-3B). Other cases identified comparable waveforms (FIG. 3C). Furthermore, while certain cases produced a singularity-like sharp peak in the GA study, this was not found with the PSO (FIG. 3D). Lastly, the waveforms in the GA study required 10000 generations to converge to the optimal waveform shape, while only 200 to 500 generations were required for the PSO to identify the optimal waveform shapes. The number of generations required for the PSO to converge are indicated under the energy value in each panel of FIG. 3.

Example 3

Optimized Periodic Waveform for Neural Block With Minimum Energy

Figure 4:
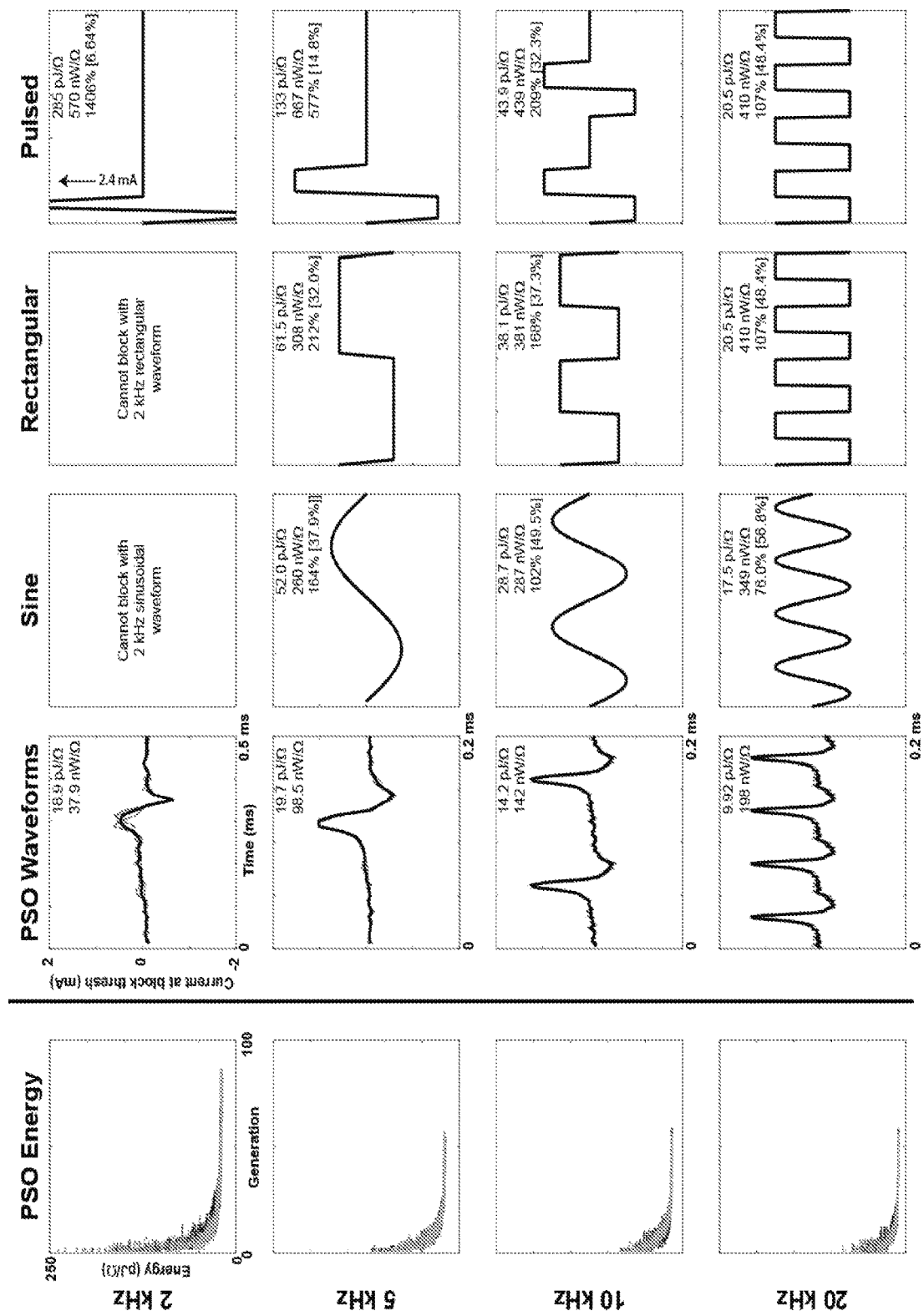
FIG. 4 includes representative results using the PSO algorithm to design charge-balanced waveforms to produce conduction block with minimum energy. Left: Best-ever energy for each of the 50 waveforms in the swarm across all generations; for example, at generation 67, the energy for waveform 12 is the lowest energy that waveform 12 has achieved over the 67 generations thus far. Energy was computed for one period of the waveform. Right: Four waveforms at block threshold for four frequencies (rows at 2, 5, 10, 20 kHz): default PSO parameter values, sine, rectangular, and pulsed with 25 µs per phase. The 2 kHz waveforms are plotted for 0.5 ms; the 5, 10, and 20 kHz waveforms are plotted for 0.2 ms. The PSO waveforms have 3 trials each show in grey, with the average shown in black. The first number in each panel is the waveform's energy over one period (T) at block threshold. The second number in each panel is the power at block threshold, to allow comparisons across frequencies. The third number in each panel with the conventional waveforms is the percent increase in energy as compared to the average PSO waveform (100%*(conventional waveform energy−PSO waveform energy)/PSO waveform energy), where a larger number indicates a greater improvement in energy efficiency with the PSO waveform. The fourth number (in square brackets) indicates the PSO energy as a percentage of the conventional waveform energy (100%*PSO waveform energy/conventional waveform energy), where a smaller number indicates a greater improvement in energy efficiency (see Table 3).

The PSO algorithm was used to design charge-balanced waveforms to produce conduction block with minimum energy when applied at 2, 5, 10, or 20 kHz. The results are shown in FIG. 4 for 2, 5, 10 and 20 kHz, including the energy-optimized charge-balanced waveforms, as well as conventional waveforms (sinusoid, rectangular, and 25 μs per phase biphasic pulses). All four optimized waveforms (2, 5, 10, and 20 kHz) had a similar shape, with a higher, narrower anodic phase, followed by a shallower, broader cathodic phase. At lower frequencies, the cathodic phase was followed by a long near-zero cathodic tail, effectively resulting in a lower duty cycle. The energy per period for all waveforms in the swarm as a function of PSO generation are shown on the left in FIG. 4, illustrating convergence of the swarm in terms of both stability of the global leader's energy. The energy for one period of each waveform at block threshold is included numerically in each panel of FIG. 4, as well as the power to facilitate comparisons across frequencies. The energies for conventional waveforms were ~75 to 1400% higher than the optimized PSO waveforms. The PSO provided a greater improvement in energy over conventional waveforms at lower frequencies. However, lower frequency waveforms required less power, except for the pulsed waveform. All PSO waveforms terminated based on convergence of the swarm, except for the 2 kHz trials which terminated based on stability of the global leader's energy. Given that it is near the block threshold frequency, the 2 kHz cases were reran for 200 ms instead of 27 ms, with a delay for the intracellular test pulses for 30 ms instead of 15 ms (to allow for a longer onset response), but the waveforms and energies were unaffected.

The average 5, 10, and 20 kHz waveforms were fit (FIG. 4) to sum of Gaussian and sum of sinusoidal equations below.

$$Ith_{est}(t) = gauss_n = a_1 * \left(\exp\left(-\left(\frac{t-b_1}{c_1}\right)^2\right)\right) +$$
$$a_2 * \left(\exp\left(-\left(\frac{t-b_2}{c_2}\right)^2\right)\right) + \ldots + a_n * \left(\exp\left(-\left(\frac{t-b_n}{c_n}\right)^2\right)\right)$$
$$Ith_{est}(t) = \sin_n = a_1 * \sin(b_1 * t + c_1) + a_2 * \sin(b_2 * t + c_2) +$$
$$\ldots + a_n * \sin(b_n * t + c_n)$$

Figure 5:
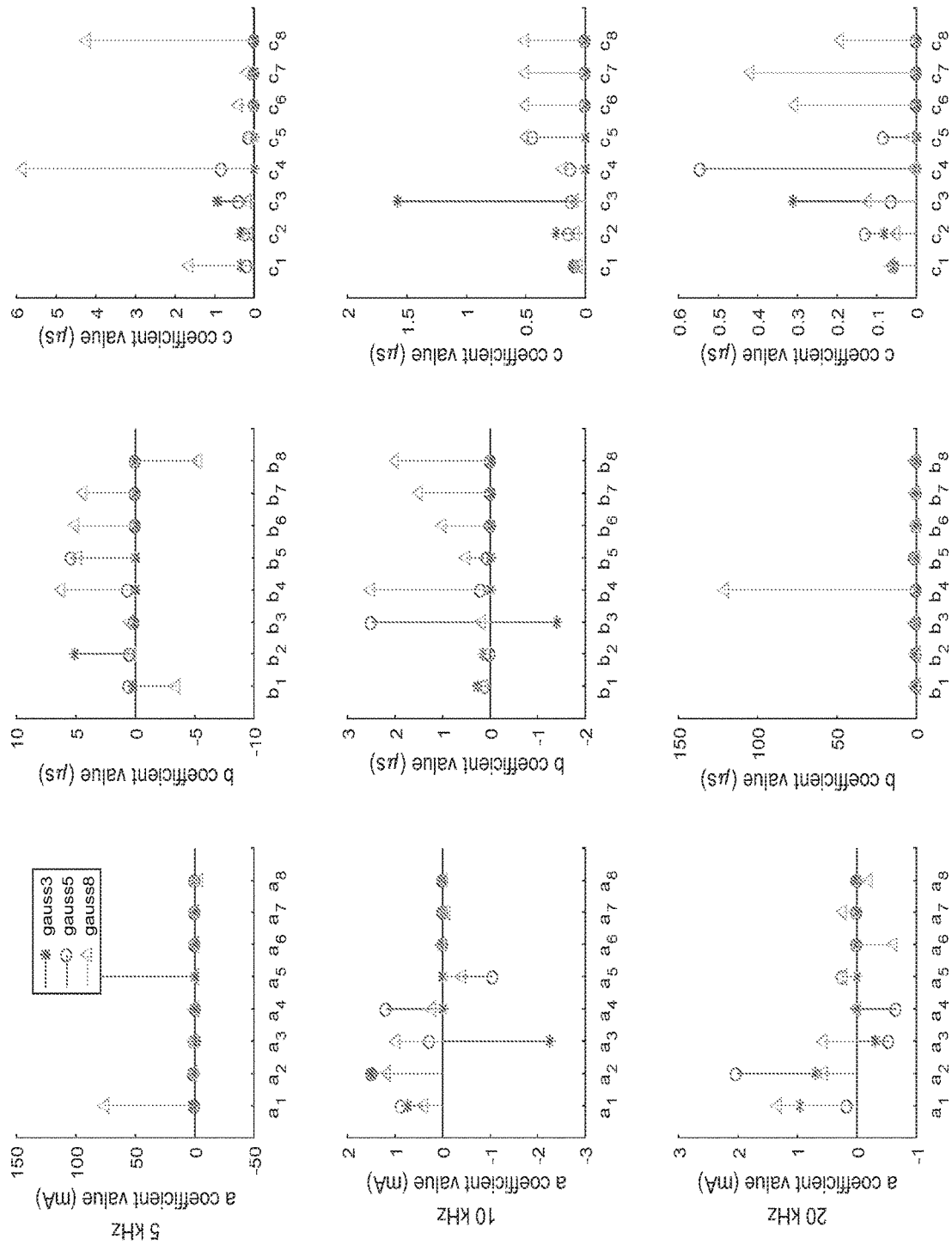
FIG. 5 includes representative coefficients resulting from the equation fits using sums of Gaussians (limits of they axes are not matched across frequencies).
Figure 6:
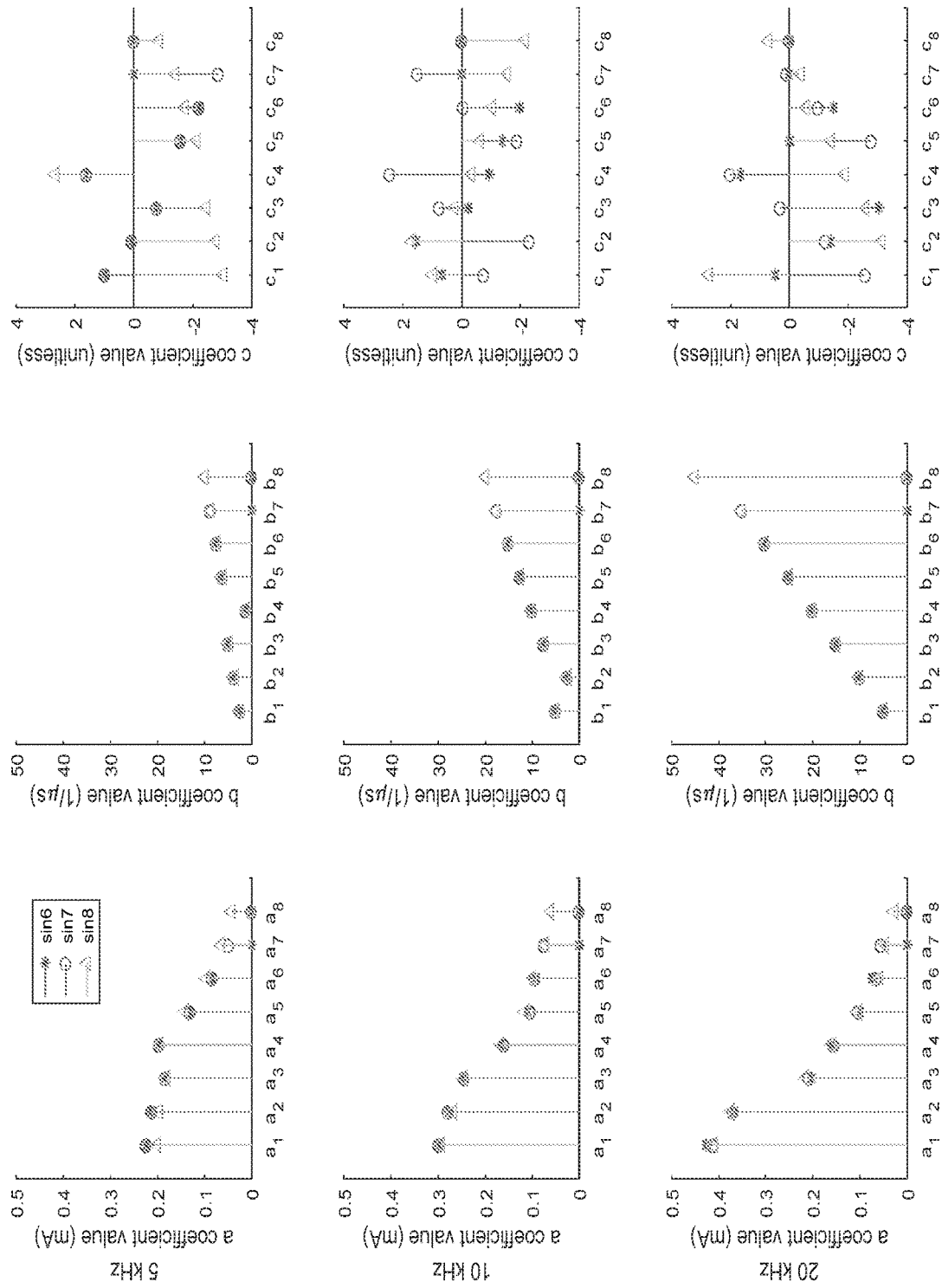
FIG. 6 includes representative coefficients resulting from the equation fits using sums of sinusoids (limits of the y axes are matched across frequencies).
Figure 7:
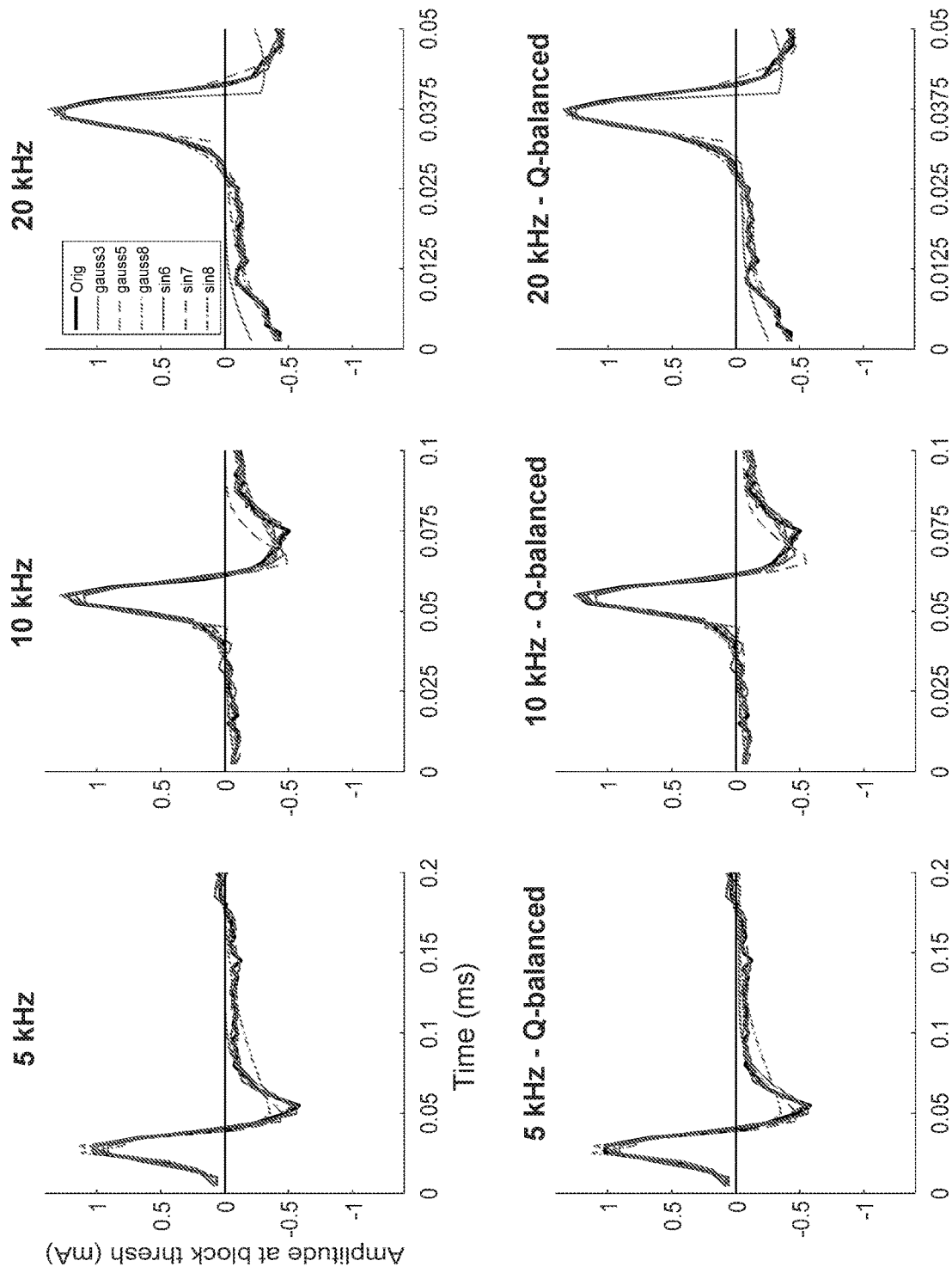
FIG. 7 includes representative equation fits to the average 5 kHz (left), 10 kHz (middle), and 20 kHz (right) waveforms using six equations. The top row shows the original fits and the bottom row shows the charge-balanced fits.
Figure 8:
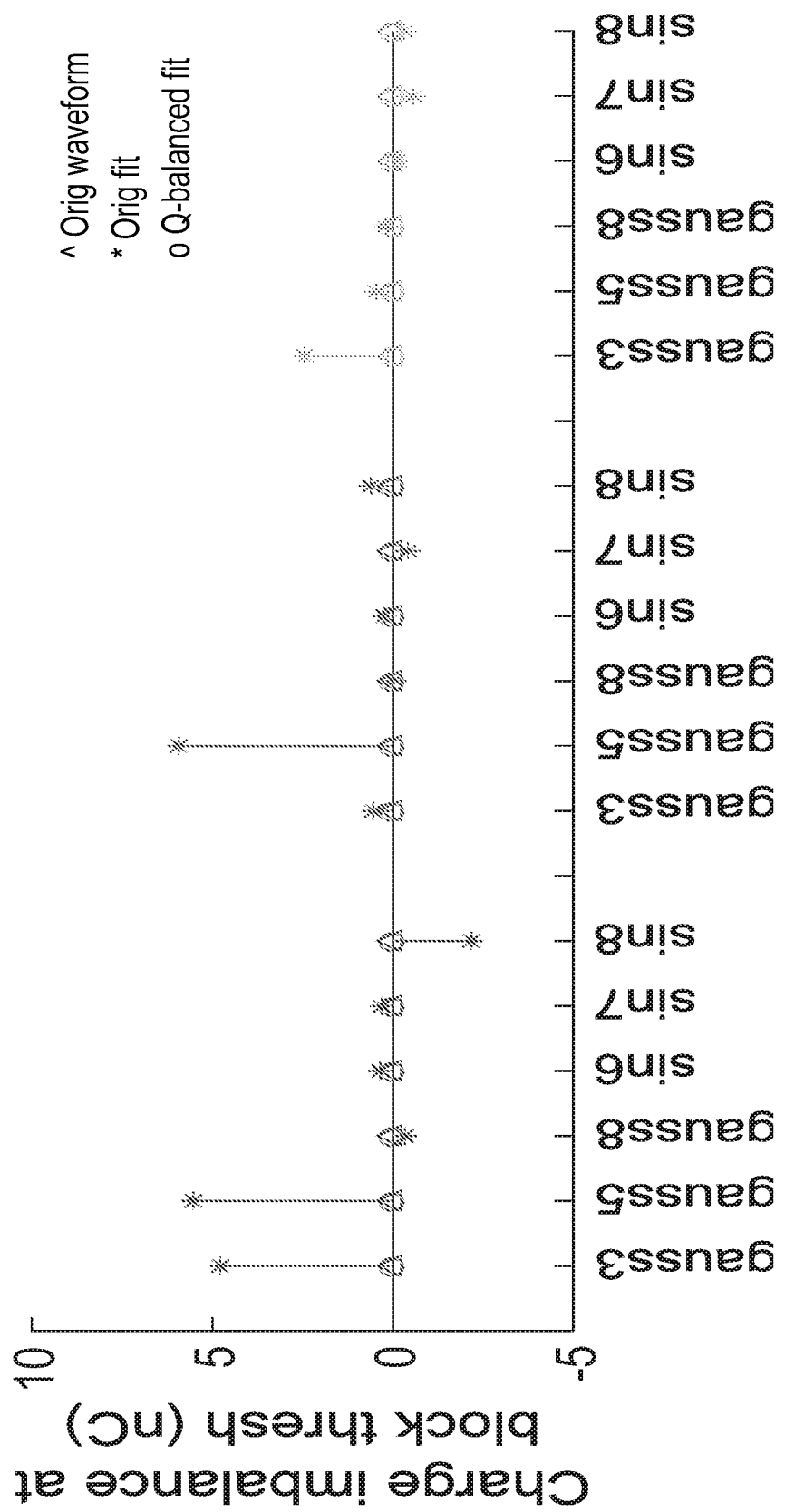
FIG. 8 includes the representative charge-imbalance of various waveforms, showing zero net charge for the original waveforms (triangles), some charge-imbalance for equations describing the waveforms (asterisks), and zero net charge when the equation fits were vertically shifted to produce charge balance (circles). The colors indicate the waveform frequencies: 5 kHz in blue, 10 kHz in red, 20 kHz in yellow.
Figure 9:
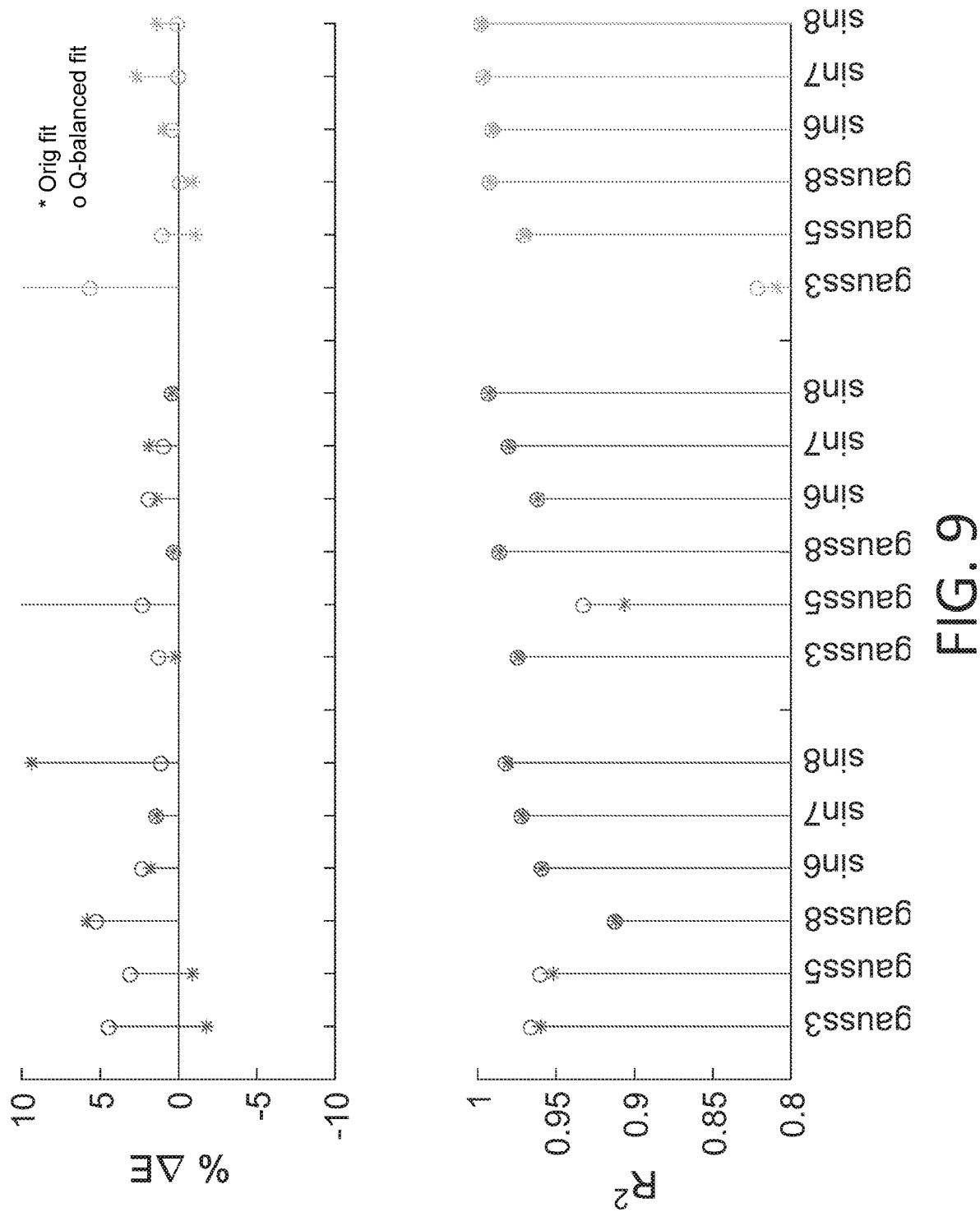
FIG. 9 includes representative results evaluating the quality of the waveform fits (asterisks) and charge-balanced fits (circles). Top: Change in waveform energy for one period at block threshold between the fit equations and the original waveform. For each frequency and equation, the original waveform was shifted to the phase at which the fit equation produced the highest $R^2$. Bottom: Coefficient of determination for each fit and charge-balanced fit.

Reasonable fits were identified using $gauss_n$ with n=3, 5, or 8, and using $sin_n$ with n=6, 7, or 8. The fits were done using nonlinear least squares with MATLAB's "fit" function. The original waveform shapes were fit using the phase-shift that produced the largest $R^2$ for each equation. The coefficients resulting from the fits are shown in FIGS. 5 and 6. The resulting fits are shown in FIG. 7 (top row). The fits had some slight charge-imbalance (FIG. 8), and thus the equation fits were also vertically translated to force charge-balance, which had little qualitative effect on the fits (FIG. 7, bottom row). The energy for one period at block threshold for each equation fit and its charge-balanced version was compared against the original waveforms (FIG. 9, top), and quantified the coefficients of determination (FIG. 9, bottom).

While the Gaussian fits described the general waveform shapes (FIG. 7, red traces), the sinusoidal equations captured the low-amplitude oscillations (FIG. 7, blue traces). The changes in threshold energy for the charge-balanced fits were mostly <5% as compared to the original waveforms. For the sinusoidal equations, the coefficients of determination were all >0.95. Given the low change in energy and high $R^2$, the sins equation was used. The b coefficients increased with kilohertz frequency, given that a higher kilohertz frequency waveform used a shorter time step. Further, the b coefficients generally increased across terms (increased sinusoidal frequency with term number). Conversely, the coefficients increased with the kilohertz frequency and decreased across terms (with decreasing sinusoidal frequency). The phase shift provided by the c coefficients did not show a clear trend for the $sin_6$ fits.

Figure 10:
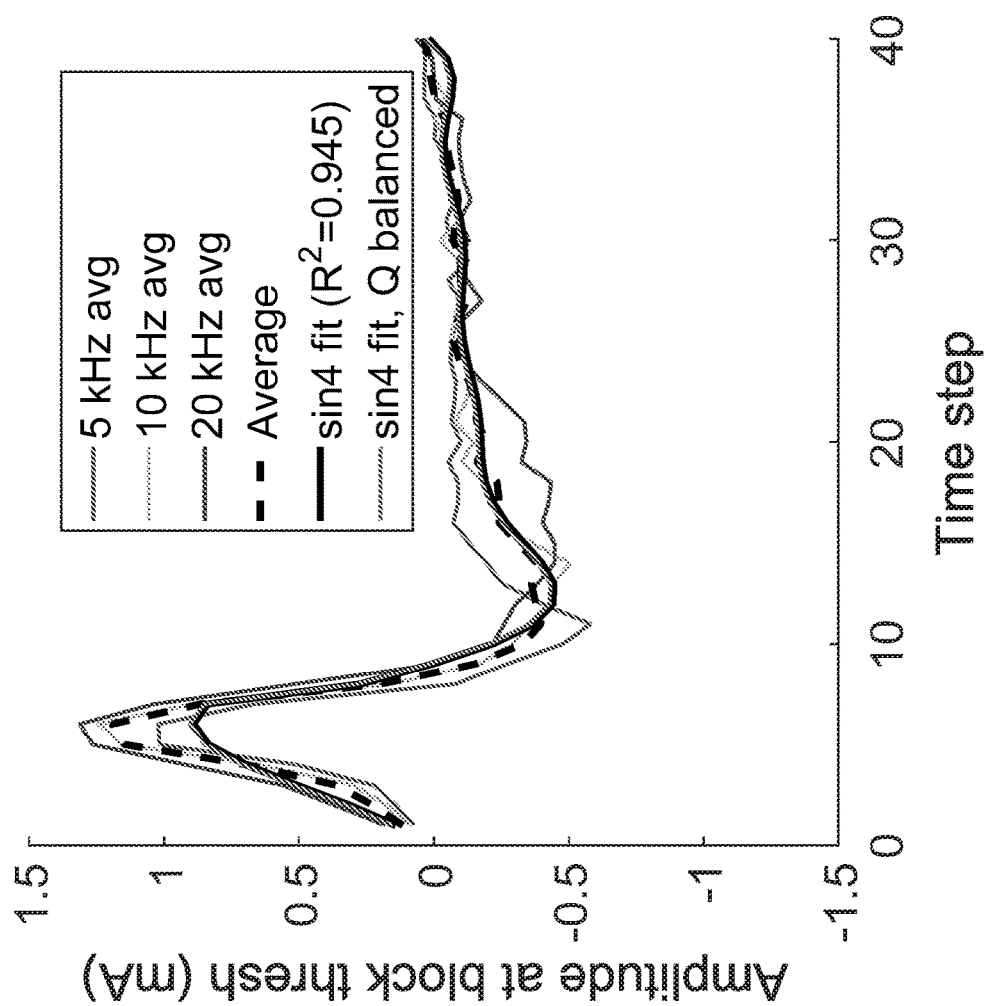
FIG. 10 includes representative waveforms with mean frequencies of 5, 10, and 20 kHz (dashed black line). The overall average waveform was fit to a $sin_4$ function (solid black line) and shifted to enforce charge balance (solid red line).

A single equation describing the identified waveforms was also obtained. Specifically, the mean 5, 10, 20 kHz waveforms used above were averaged (FIG. 10), dashed black line) and their time point indices 1 to 40 were used as the abscissa, rather than time, given their different time steps. In one example, the averaged waveforms were fit to a $sin_4$ function, and produced the following equation:

$$Ith_{est}(i) =$$
$$sin_4 = 0.321 \text{ mA} * \sin(0.158 * i + 2.25) + 0.324 \text{ mA} * \sin(0.307 * i + 2.42) +$$
$$0.238 \text{ mA} * \sin(0.451 * i + 2.68) + 0.105 \text{ mA} * \sin(0.579 * i + 3.35)$$

where i is the time point index from 1 to 40. Through variable substitution, the time point index can be converted such that the equation describes one period of the waveform as a function of time and frequency (f=1/T), since one period (T) of the waveform is described by 40 time steps:

$$dt = \frac{T}{40}$$

$$i = \frac{t}{dt} = t * \frac{40}{T} = t * 40 * f$$

$$Ith_{est}(t, f) = \sin_n = 0.321 \text{ mA} * \sin(0.158 * t * 40 * f + 2.25) +$$

$$0.324 \text{ mA} * \sin(0.307 * t * 40 * f + 2.42) +$$

$$0.238 \text{ mA} * \sin(0.451 * t * 40 * f + 2.68) +$$

$$0.105 \text{ mA} * \sin(0.579 * t * 40 * f + 3.35)$$

where t spans dt=T/40 to T=1/f, using any time increment that provides sufficient resolution; t and f must have reciprocal units. The resulting waveform (as a function of time step i) is shown in FIG. 10 (solid black line). The fit equation was also vertically shifted to achieve charge balance (FIG. 10, red line). The charge imbalance depends on the kilohertz frequency at which the waveform is delivered, since a lower kilohertz frequency has a longer time step: −2.55 nC for 5 kHz, −1.28 nC for 10 kHz, and −0.638 nC for 20 kHz. Comparing the energy for one period at block threshold between the original waveforms and the charge-balanced fit equation yielded 3.8, 2.8, and 0.4% difference for 5, 10, and 20 kHz, respectively.

Example 4

PSO Algorithm Sensitivity Analysis

Figure 11:
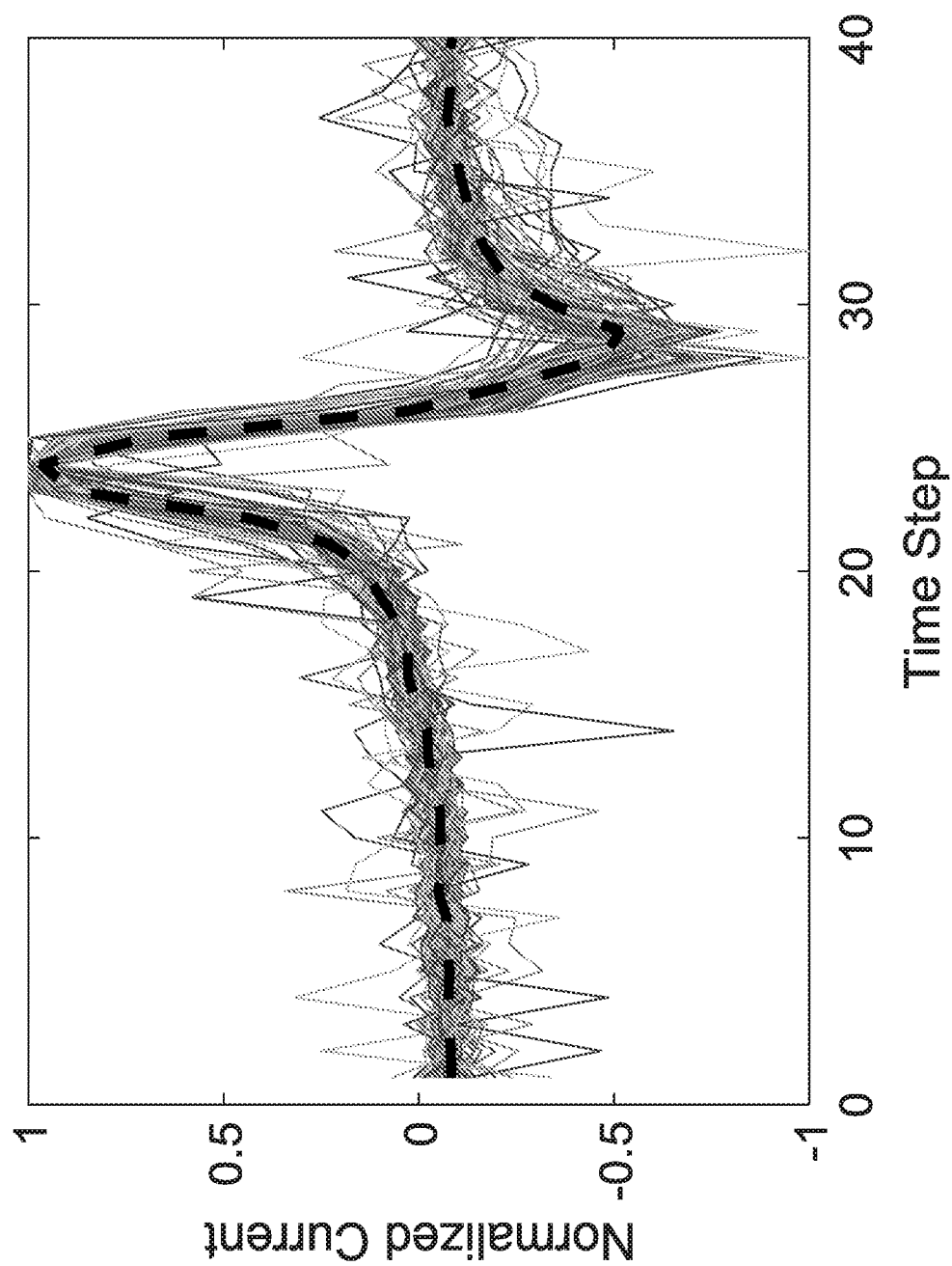
FIG. 11 includes representative overlays of all sensitivity analysis waveforms from trials of the PSO with different parameter values to compare their shapes. Each waveform was temporally shifted to maximize the cross-correlation with a single arbitrary waveform.

Sensitivity analyses were conducted on the parameters of the PSO algorithm to ensure robustness of the identified optimized waveforms and to explore potential improvements of the algorithm's performance (rate of convergence), and thereby developed two iterations of the algorithm (Table 3). Block thresholds with 5 kHz waveforms were investigated. For the initial default parameters, values were selected that achieved effective performance during preliminary algorithm development. One parameter at a time was then varied and the minimum energy required to achieve neural block at 5 kHz was recorded for three trials per parameter set, after which final parameter values were identified. Waveform initialization was random for each trial. Parameters related to network topology, to the velocity equation, and to the termination criteria were investigated, in addition to a few miscellaneous parameters (Table 3). In these analyses, relative performance was quantified by comparing the minimum energy recorded in each trial to the average energy required to achieve block using default parameters across three trials. The total number of generations required to attain one of the termination criteria was also recorded, as well as the generation number at which the final waveform was identified. For the initial simulations with default parameters, optimal waveforms with energies of 19.4, 19.8, and 19.9 pJ/Ω (mean=19.7 pJ/Ω) were obtained. Across all parameter changes, approximately the same optimal waveform shape was obtained (FIG. 11).

TABLE 3

PSO parameters used in two versions of the algorithm and associated sensitivity analyses. The default values are bolded and underlined. The initial parameter values were based on preliminary trials during algorithm development.

| Parameter | Initial PSO | Final PSO |
|---|---|---|
| Topology | | |
| Number of neighborhoods (50 waveforms total) | 10, <u>5</u>, 2, 1 | 5 |
| Waveforms in swarm [min total # evaluations] (Minimum of 50 generations, including 25 stability generations, 5 neighborhoods) | 25 [1,250], <u>50 [2,500]</u>, 125 [6,250] | 50 |
| Waveforms in swarm/min # generations/stability generations/cross-correlation realignment interval (5 neighborhoods; minimum 2,500 total evaluations) | 25/100/50/20, <u>50/50/25/10</u>, 125/20/10/4 | 50/50/25/10 |
| Velocity Equation | | |
| Swarm velocity coefficient ($w_2$) | 0.75, <u>1.5</u>, 3 | 1.5 |
| Termination | | |
| Minimum number of generations | 25, <u>50</u>, 100, 125 | 50 |
| Minimum stability generations | 10, <u>25</u> | 25 |
| Stability threshold | <u>1</u>, 2% | 1% |
| Swarm convergence threshold | 0.5, <u>1</u>, 2% | 1% |
| Other | | |
| Cross-correlation realignment interval | 1, 5, <u>10</u>, 25, Never | Never |
| Waveform resolution (dt) | 1.25, <u>5</u> μs | 5 μs |
| Cost function (E = energy; Balance = sum of all time points; Mag = sum of magnitude of all time points) | <u>E</u>; E+\|E*balance/mag\| | E |
| Nerve Morphology | | |
| Electrode-fiber distance | 0.5, <u>1</u>, 1.5 mm | 1 mm |
| Fiber diameter | 10, <u>16</u> μm | 16 μm |

Topology. The winner-takes-all PSO neighborhood topology was evaluated by varying the number of neighborhoods (maintaining a swarm of 50 waveforms, thereby varying the number of waveforms per neighborhood) and the total number of waveforms in the swarm (maintaining the number of neighborhoods at 5, thereby varying the number of waveforms per neighborhood). The total number of waveforms were evaluated in two ways: first, the minimum number of generations was maintained at 50; second, the total minimum number of waveforms evaluated by compensating for changes in swarm size with changes in the minimum number of generations, the number of stability generations, and the number of generations were maintained between cross-correlation realignments. For example, with the default parameter values, 50 waveforms in the swarm were used and a minimum of 50 generations, resulting in at least 50*50=2,500 waveform evaluations. If instead 25 waveforms were used in the swarm, the minimum number of generations was adjusted to 100 to maintain a total minimum of 2,500 waveform evaluations; also, 50 stability generations were used instead of 25 and the swarm's waveforms were realigned every 20 generations instead of every 10.

Figure 12:
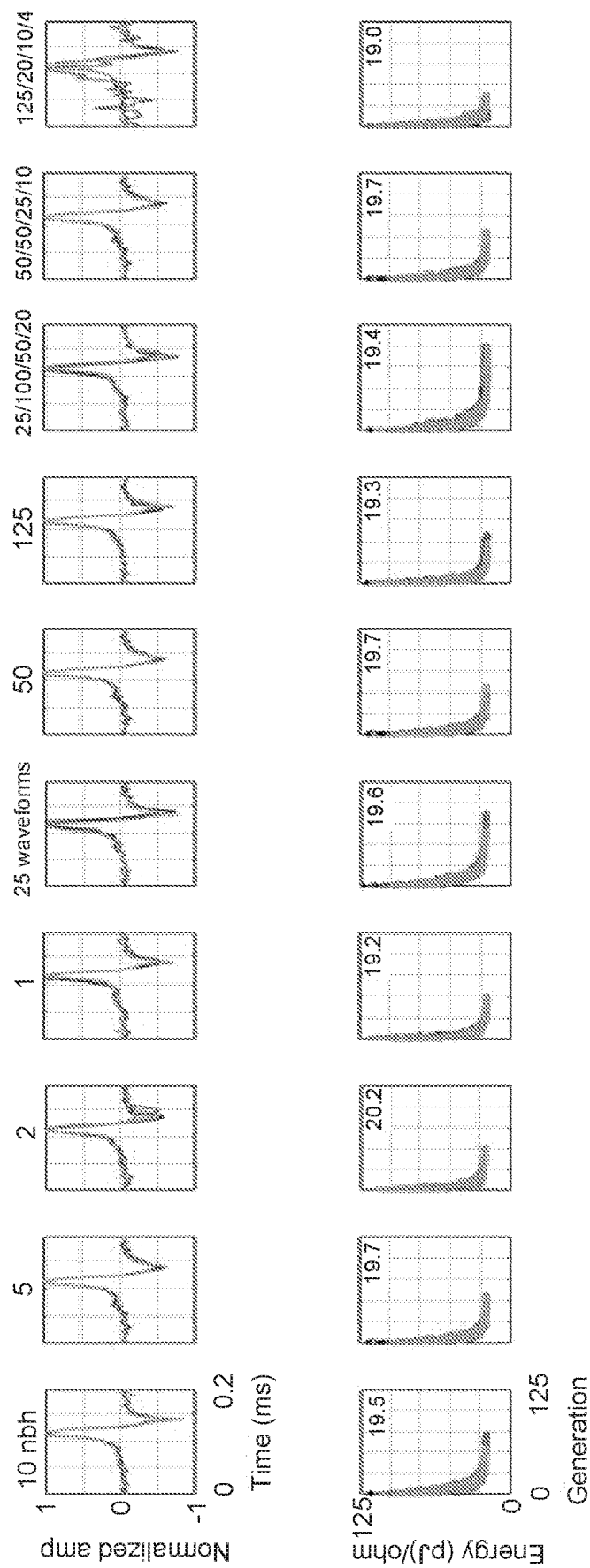
FIG. 12 includes representative data from topology sensitivity analyses. Top row: Waveforms from three trials of each parameter set (black, red, green), phase shifted to align with a reference waveform across all sensitivity analyses. Bottom row: Best-ever (lowest) block threshold energy for one period of each waveform in the swarm as a function of generation from three trials of each parameter set. The value in the top right corner in each panel indicates the mean block threshold energy of the lowest-energy waveform from each trial.
Figure 13:
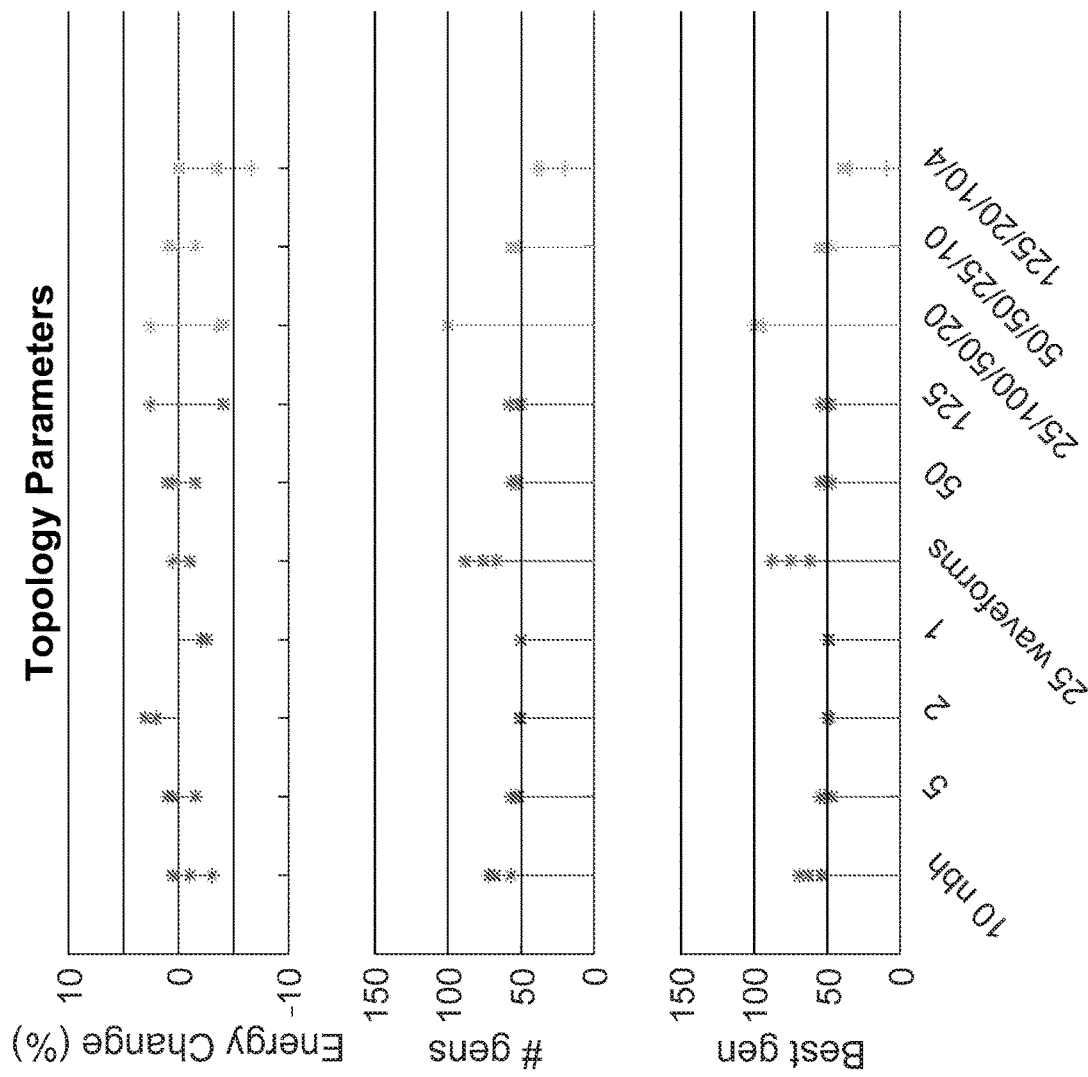
FIG. 13 includes representative output measures for topology sensitivity analyses (see Table 3). Different numbers of neighborhoods (nbh's) were calculated amongst which the 50 waveforms were divided (blue), different numbers of waveforms divided into 5 neighborhoods (red), and different numbers of waveforms divided into 5 neighborhoods while maintaining the total number of waveform evaluations up to the minimum number of generations and the number of evaluations between cross-correlation realignments (yellow; tick labels indicate number of waveforms/minimum number of generations/number of stability waveforms for termination/cross-correlation alignment interval). Top row: Percent changes in energy referenced to the mean energy across 3 trials with the default parameters. Middle row: Total number of generations (≥50) to attain the termination criteria. Bottom row: Generation number at which the final waveform was obtained.

The results are shown in FIGS. 12 and 13. All waveforms except one (discussed below) and all energy vs. generation (EvG) curves were smooth (FIG. 12). Changing the number of neighborhoods had little impact on the results. Using more (10) neighborhoods resulted in slightly lower energy (and slightly slower termination), while using fewer neighborhoods could either produce slightly higher (2 neighborhoods) or lower (1 neighborhood) energy.

Reducing the number of waveforms required more generations to terminate, as expected. Increasing the number of waveforms had a larger variability in the final energy. Similar results were obtained with changing the number of waveforms in tandem with the minimum number of generations, number of stability generations, and cross-correlation interval, although one trial with 125 waveforms was noisy (FIG. 12); unlike all other trials in the topology sensitivity analyses, that trial terminated based on attaining the number of stability generations (since only 10 were required), while the other trials achieved swarm convergence.

Overall, these data suggested maintaining all topology parameter values. The only topology parameter that resulted in improved energy and more rapid convergence was using 125 waveforms with only 20 minimum generations, 10 stability generations, and cross-correlation realignment every 4 generations; however, one of three trials produced a waveform with increased noise.

Figure 14:
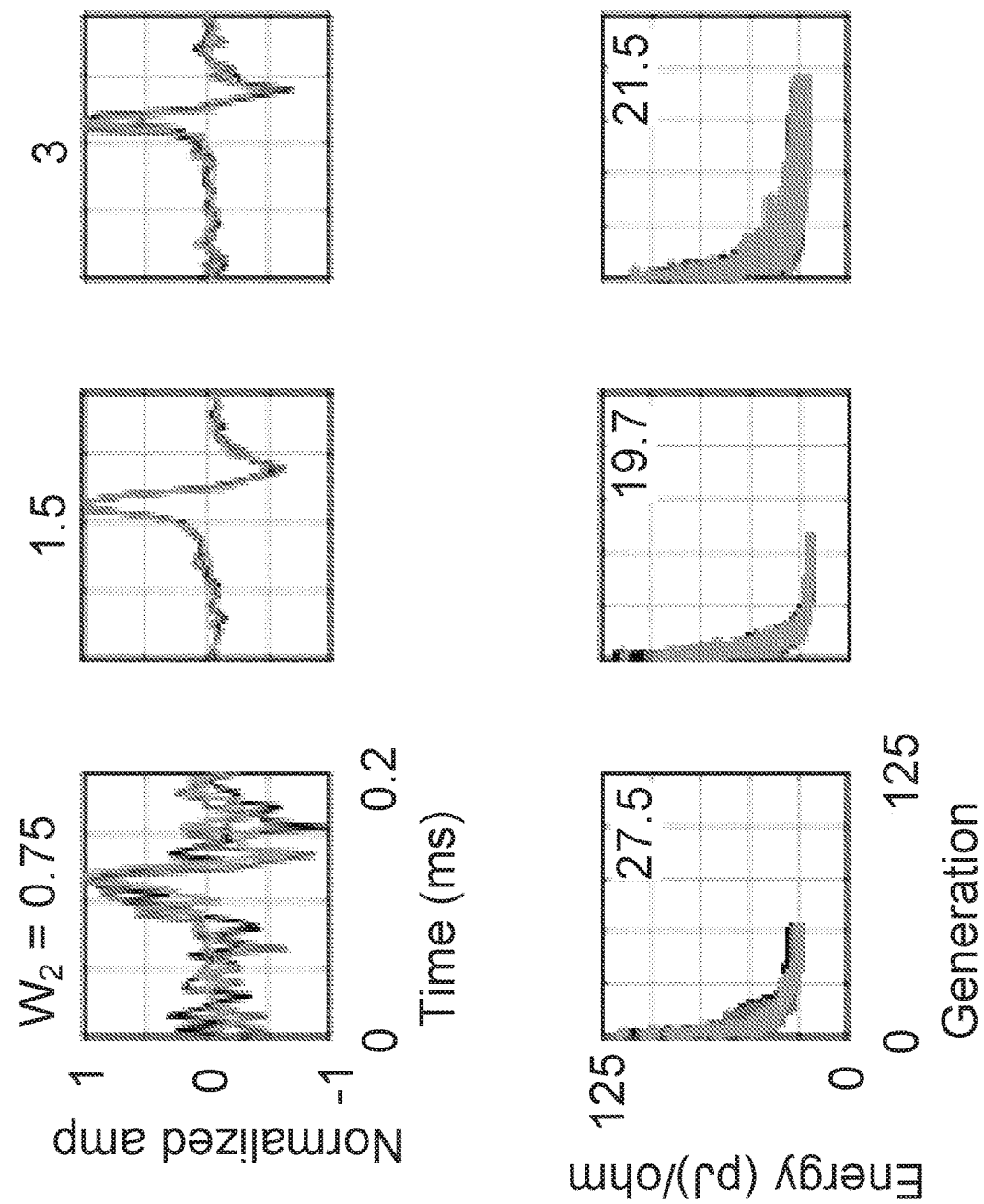
FIG. 14 includes representative data from velocity sensitivity analyses. Top row: Waveforms from three trials of each parameter set (black, red, green), phase shifted to align with a reference waveform across all sensitivity analyses. Bottom row: Best-ever (lowest) block threshold energy for one period of each waveform in the swarm as a function of generation from three trials of each parameter set. The value in the top right corner in each panel indicates the mean block threshold energy of the lowest-energy waveform from each trial.
Figure 15:
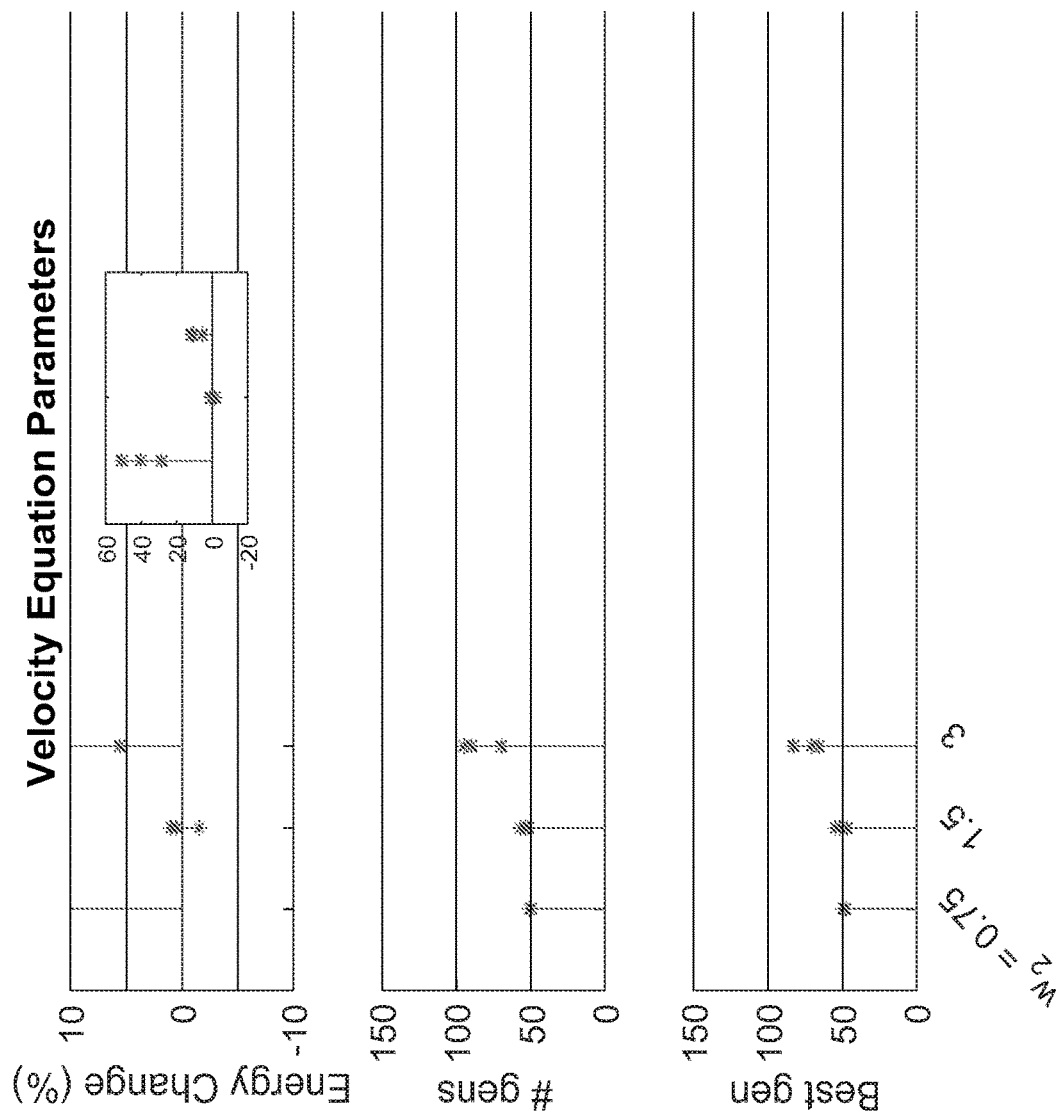
FIG. 15 includes representative output measures for velocity sensitivity analyses (see Table 3). Three values were evaluated for the $w_2$ coefficient in the velocity equation. Top row: Percent changes in energy referenced to the mean energy across 3 trials with the default parameters. Middle row: Total number of generations (≥50) to attain the termination criteria. Bottom row: Generation number at which the final waveform was obtained.

Velocity Equation. Sensitivity analyses were conducted on the value of the $w_2$ coefficient of the velocity equation. The results are shown in FIGS. 14 and 15. The block threshold energy was substantially higher when $w_2$ was halved or doubled. When $w_2$ was halved to 0.75, the final waveforms were noisy (FIG. 14), suggesting that the movement of time point amplitudes towards the influencing waveforms was insufficient; when $w_2$ was doubled to 3, the additional generations were required to terminate and terminate was achieved based on achieving stability threshold rather than swarm convergence. Thus, these data suggested maintaining $w_2$ at its original value of 1.5.

Termination. The effects of the termination criteria were also evaluated by varying the minimum number of generations, the number of stability generations (minimum number of generations over which the change in energy of the global leader must be within the stability threshold), the stability threshold (percent difference between the lowest and highest global leader energies during the stability generations), and the convergence threshold (percent difference in energy between the waveforms with the highest and lowest best-ever energies for the current generation). If either the stability criterion or the convergence criterion is met at the minimum number of generations, the algorithm is terminated; otherwise, one generation was added at a time until one of the criteria is met.

Figure 16:
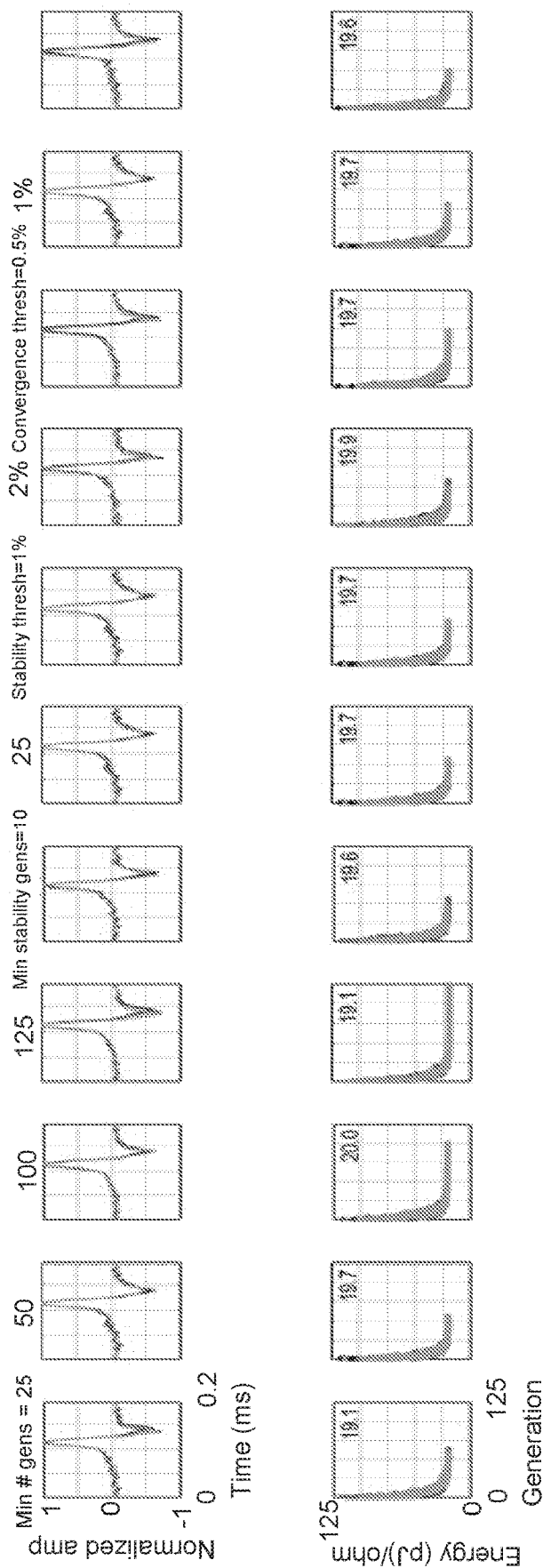
FIG. 16 includes representative data from termination criteria sensitivity analyses. Top row: Waveforms from three trials of each parameter set (black, red, green), phase shifted to align with a reference waveform across all sensitivity analyses. Bottom row: Best-ever (lowest) block threshold energy for one period of each waveform in the swarm as a function of generation from three trials of each parameter set. The value in the top right corner in each panel indicates the mean block threshold energy of the lowest-energy waveform from each trial.
Figure 17:
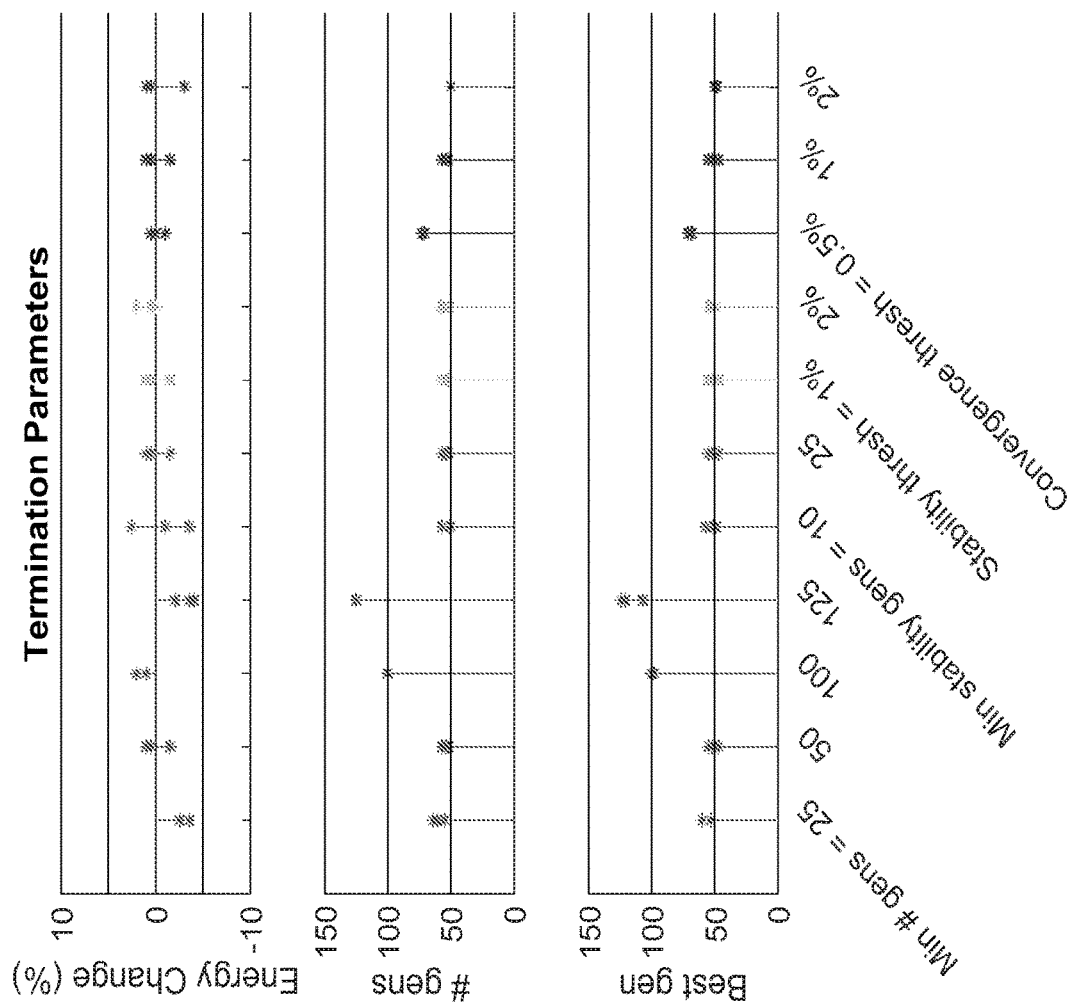
FIG. 17 includes representative output measures for termination criteria sensitivity analyses (see Table 3). The effects of the minimum number of generations, the minimum number of stability generations, the stability threshold (percent difference between the lowest and highest global leader energies during the stability generations), and the convergence threshold (percent difference in energy between the waveforms with the highest and lowest best-ever energies for the current generation) were evaluated. Top row: Percent changes in energy referenced to the mean energy across 3 trials with the default parameters. Middle row: Total number of generations (≥50, except with changes in the minimum number of generations) to attain the termination criteria. Bottom row: Generation number at which the final waveform was obtained.

The results are shown in FIGS. 16 and 17. All waveforms and all EvG curves were smooth (FIG. 16). It was found that both increasing and decreasing the number of generations could result in decreased energy, reflecting variability across trials. Decreasing the number of stability generations increased the variability across trials, as suggested by the topology sensitivity analyses; it also caused the algorithm to terminate based on stability rather than swarm convergence. Doubling the stability threshold from 1 to 2% had little effect. Most trials across the sensitivity analyses terminated based on swarm convergence; when a more rigorous swarm convergence of 0.5% was used instead of 1%, the swarm instead terminated based on stability after requiring additional generations, without energy improvements. Doubling the convergence threshold to 2% had little effect. Overall, these data suggested maintaining all parameter values for the termination criteria.

Figure 18:
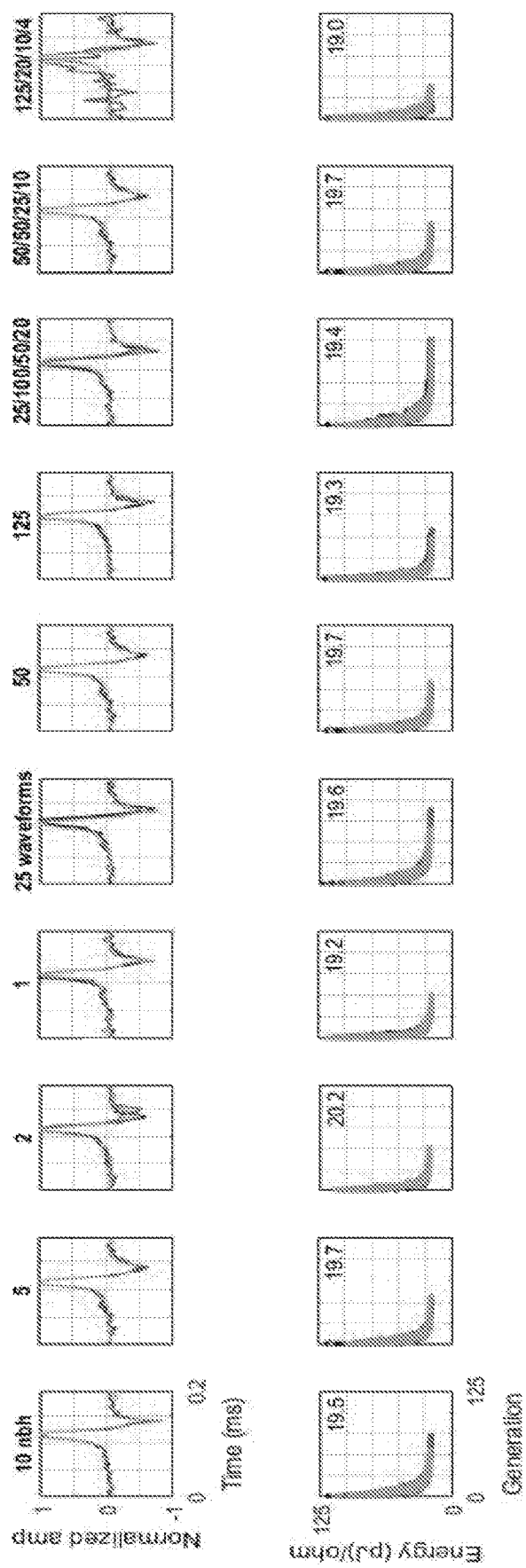
FIG. 18 includes representative data from topology sensitivity analyses. Top row: Waveforms from three trials of each parameter set (black, red, green), phase shifted to align with a reference waveform across all sensitivity analyses. Bottom row: Best-ever (lowest) block threshold energy for one period of each waveform in the swarm as a function of generation from three trials of each parameter set. The value in the top right corner in each panel indicates the mean block threshold energy of the lowest-energy waveform from each trial.
Figure 19:
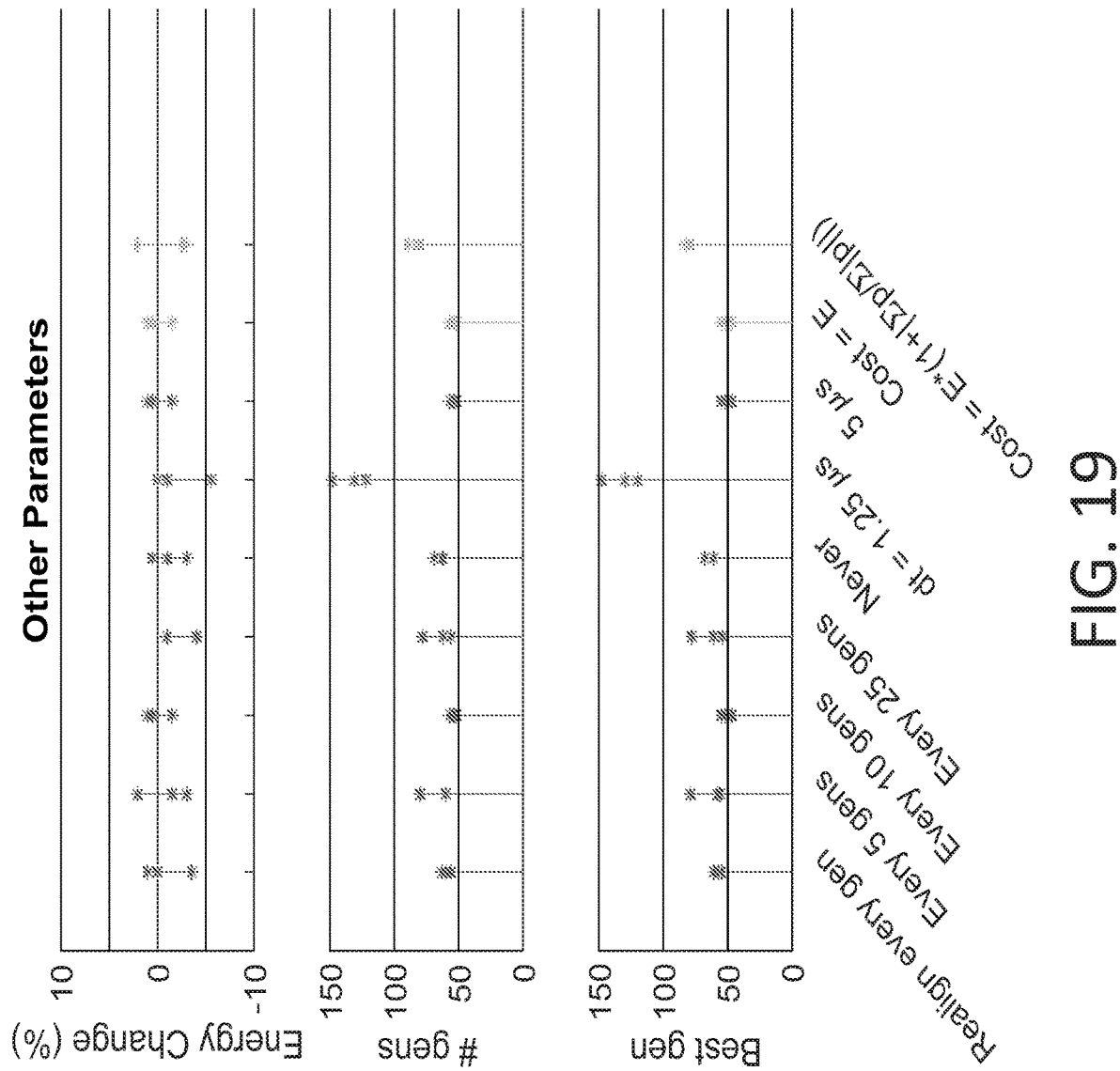
FIG. 19 includes representative output measures for sensitivity analyses on other parameters, including cross-correlation realignment interval (blue), time step (red), and cost function (yellow) (see Table 3). Top row: Percent changes in energy referenced to the mean energy across 3 trials with the default parameters. Middle row: Total number of generations (≥50) to attain the termination criteria. Bottom row: Generation number at which the final waveform was obtained.

Other Parameters. The effects of varying the cross-correlation realignment interval, the time step, and the cost function were evaluated. The results are shown in FIGS. 18 and 19. As described further herein, the waveforms were periodically realigned by maximizing the cross-correlation of each waveform with the global leader. It was found that whether every generation was realigned, never realigned, or realigned at an intermediate frequency, the energy and rate of convergence were unaffected. All trials terminated based on swarm convergence.

The effects of the time step (dt) were also evaluated. Note that the time step affects the definition of each waveform in the PSO and affects the spatiotemporal simulation of the model axon in NEURON. In the default case, each 5 kHz waveform had 40 time points with dt=5 μs. Decreasing dt to 1.25 μs increased temporal resolution in NEURON and quadrupled the number of time points required to represent one period at 5 kHz, thereby quadrupling the number of dimensions to be optimized each generation. Given the additional degrees of freedom, the swarm required longer to converge, although only ~150% more generations were needed, rather than ~400%. Further, the energy of the final waveforms were comparable to the results with d=5 μs.

Finally, rather than simply using the energy as the cost function to identify the influencing waveforms and then forcing charge balance once the amplitudes are updated with the velocity equation, an alternative cost function was evaluated that incorporates both energy and charge-balance (see equation below):

$$\text{Cost} = E + \text{abs}\left(E * \frac{\text{balance}}{\text{mag}}\right)$$

where balance is the sum of all the time points for a given waveform and mag is the sum of the absolute value for all the time points for a given waveform. The swarm required more generations to terminate and in two of the three trials, it terminated based on the stability threshold rather than swarm convergence. However, it nevertheless resulted in the same qualitative, smooth waveform shape, albeit with charge imbalances of −5, 60, and 36 pC per phase for the three trials.

Overall, it was found that the cross-correlation realignment was unnecessary, that a decreased time step still produced smooth waveforms and only slightly prolonged termination, and that charge-balance may be nearly obtained through the cost function rather than through manual enforcement.

Figure 20:
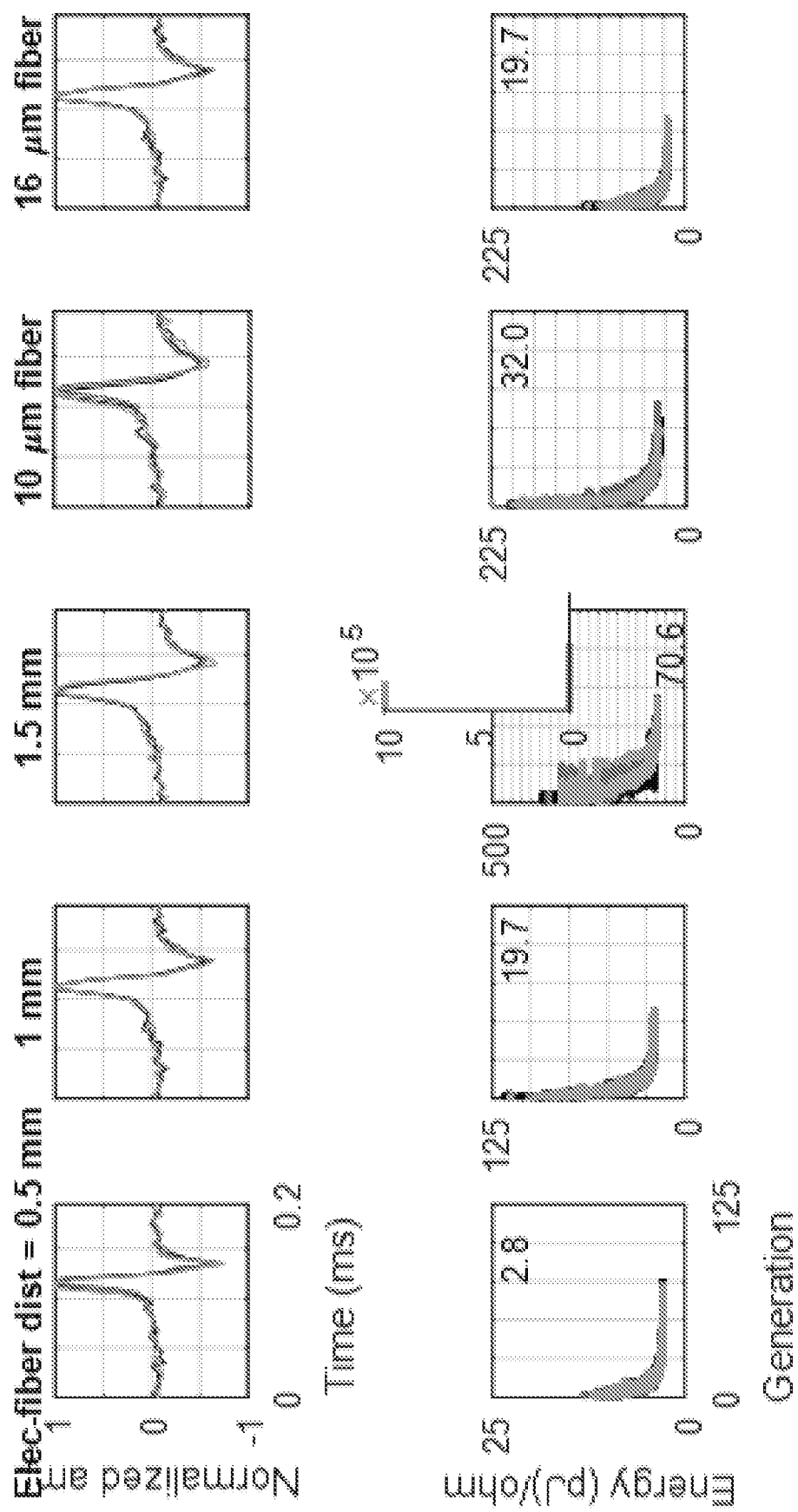
FIG. 20 includes representative data from nerve morphology sensitivity analyses. Top row: Waveforms from three trials of each parameter set (black, red, green), phase shifted to align with a reference waveform across all sensitivity analyses. Bottom row: Best-ever (lowest) block threshold energy for one period of each waveform in the swarm as a function of generation from three trials of each parameter set. The value in the top right corner in each panel indicates the mean block threshold energy of the lowest-energy waveform from each trial.
Figure 21:
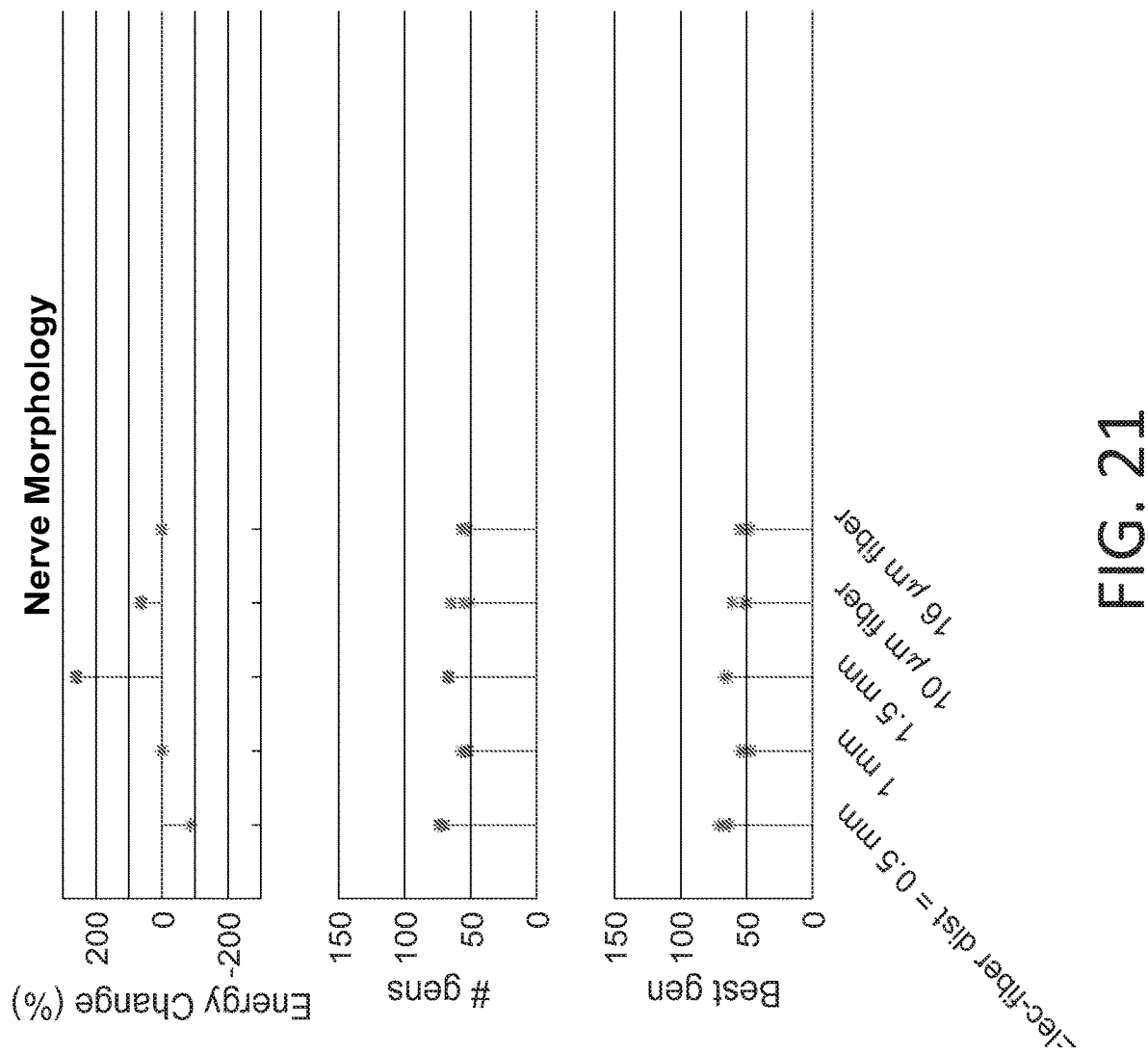
FIG. 21 includes representative output measures for nerve morphology sensitivity analyses, including the electrode-fiber distance (distance from the point source placed over the middle node of Ranvier to the middle node of Ranvier) and the diameter of the myelinated model axons. Top row: Percent changes in energy referenced to the mean energy across 3 trials with the default parameters. Middle row: Total number of generations (≥50) to attain the termination criteria. Bottom row: Generation number at which the final waveform was obtained.

Nerve Parameters. The PSO was also run with a smaller fiber diameter and different electrode-fiber distances. Results are shown in FIGS. 20 and 21. Halving the default distance of 1 mm required 85.8% less energy, while increasing the distance from 1 to 1.5 mm required 258% more energy. Reducing the fiber diameter to 10 μm increased energy demands, requiring 62.4% more energy than waveforms optimized for 16 μm fibers. All trials terminated based on swarm convergence and required similar numbers of generations. All waveforms across all generations for all trials for all sensitivity analyses successfully produced block, except for a few early-generation waveforms with the 1.5 mm electrode-fiber distance, likely due to insufficient upper bound on the binary search algorithm.

Exploration Term. The effects of an additional term in the velocity equation that provided exploration was evaluated using each particle's previous locations as well as an additive random term (see equation below):

$$\overrightarrow{v_{j,k+1}} = w_{1,k} * \left[\overrightarrow{v_{j,k}} + U(-0.2, 0.2)\right] +$$
$$w_2 * \left[\left(\overrightarrow{p_{l1,k}} - \overrightarrow{p_{j,k}}\right) * U(0, 1) + \left(\overrightarrow{p_{l1,k}} - \overrightarrow{p_{j,k}}\right) * U(0, 1) + U(0, 0)\right]$$

This inertial/exploration $w_1$ term could prevent premature convergence and promote global exploration. The inertial term contains information about a particles' past velocities, as well as a zero-mean, uniform random term, allowing further exploration in case the particle velocity v approaches zero prematurely. The weighting ($w_1$) of this inertial term, a value greater than or equal to zero, helped ensure that the particle velocity would not converge prematurely or diverge, which would result in suboptimal solutions. The value of $w_1$ was specific for each neighborhood for each generation according to the average particle velocity, a metric directly related to the particles' average distance from the best solutions; the neighborhood-specific $w_1$ values provided freedom for each neighborhood to explore their space as long as needed and to converge on their optimal solution at an appropriate time for their neighborhood. $w_1$ was initialized to $v_{init}=v_{ideal,1}$ and updated to produce a decreasing average neighborhood velocity across generations, improving performance as divergence and premature convergence are avoided. $v_{ideal,k}$ was then decreases with each generation such that it reached zero at the minimum number of generations (50 generations), encouraging convergence. For each neighborhood at each generation k, if the neighborhood's average particle velocity ($v_{avg,k}$) was more than 5% away from $v_{ideal,k}$, then $w_{1,k}$ was adjusted from its previous estimate (see equation below):

if $(v_{avg,k} > 1.05 * v_{ideal,k}) \| (v_{avg,k} < 0.95 * v_{ideal,k})$ $$w_{1,k} = \left(\frac{v_{ideal,k}}{v_{avg,k}}\right) * w_{1,k-1}$$

else $$w_{1,k} = w_{1,k-1}$$

Thus, each neighborhood of the swarm was updated independently, each with its own inertial weighting coefficient $w_1$. This design choice prevented convergence in some neighborhoods from causing $w_1$ to increase across all neighborhoods, which in turn would cause an increase in average velocity and potential divergence in neighborhoods that have not yet converged.

Figure 22:
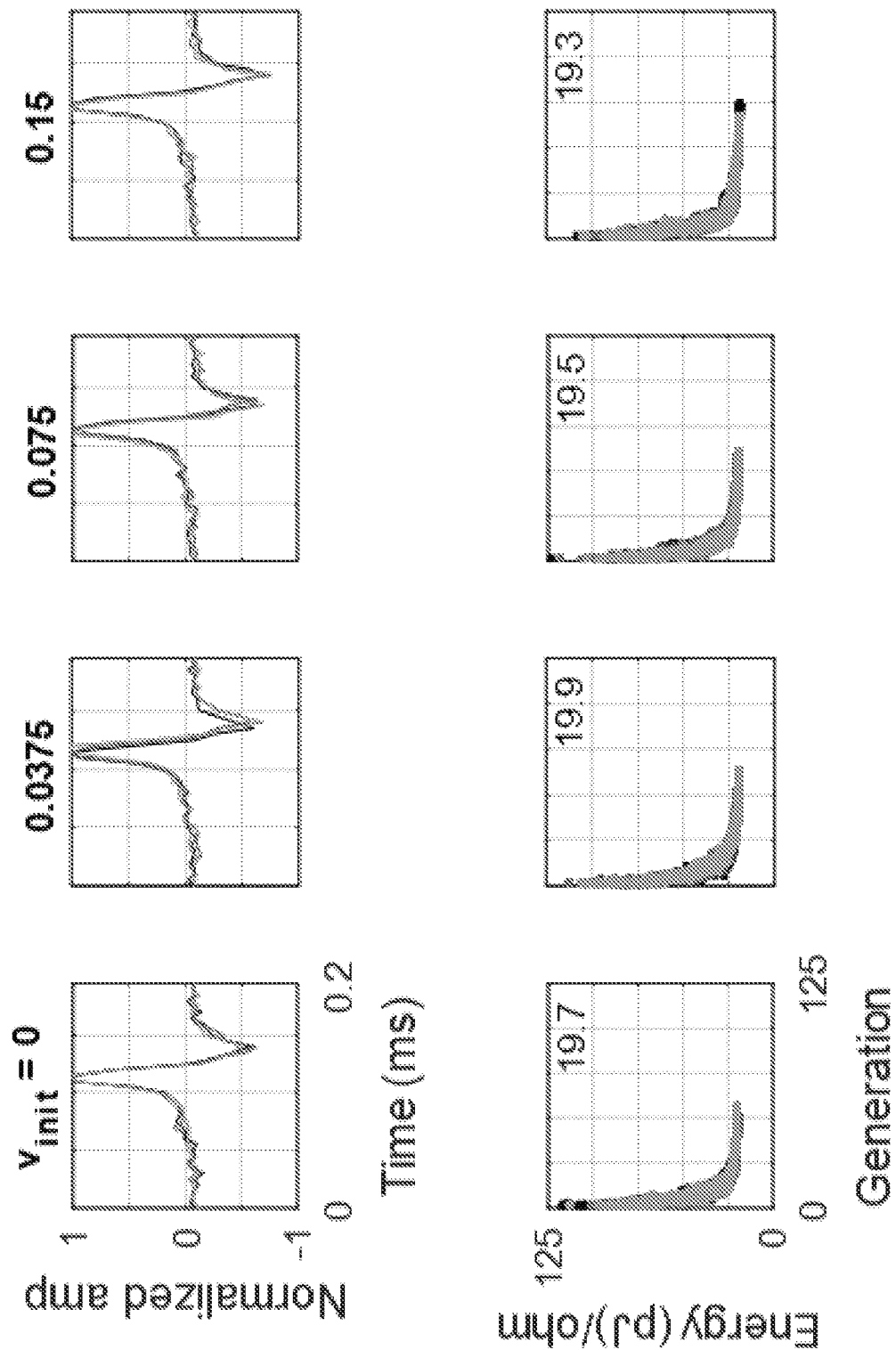
FIG. 22 includes representative data from sensitivity analyses on the addition of an exploration term to the velocity equation. Top row: Waveforms from three trials of each parameter set (black, red, green), phase shifted to align with a reference waveform across all sensitivity analyses. Bottom row: Best-ever (lowest) block threshold energy for one period of each waveform in the swarm as a function of generation from three trials of each parameter set. The value in the top right corner in each panel indicates the mean block threshold energy of the lowest-energy waveform from each trial.
Figure 23:
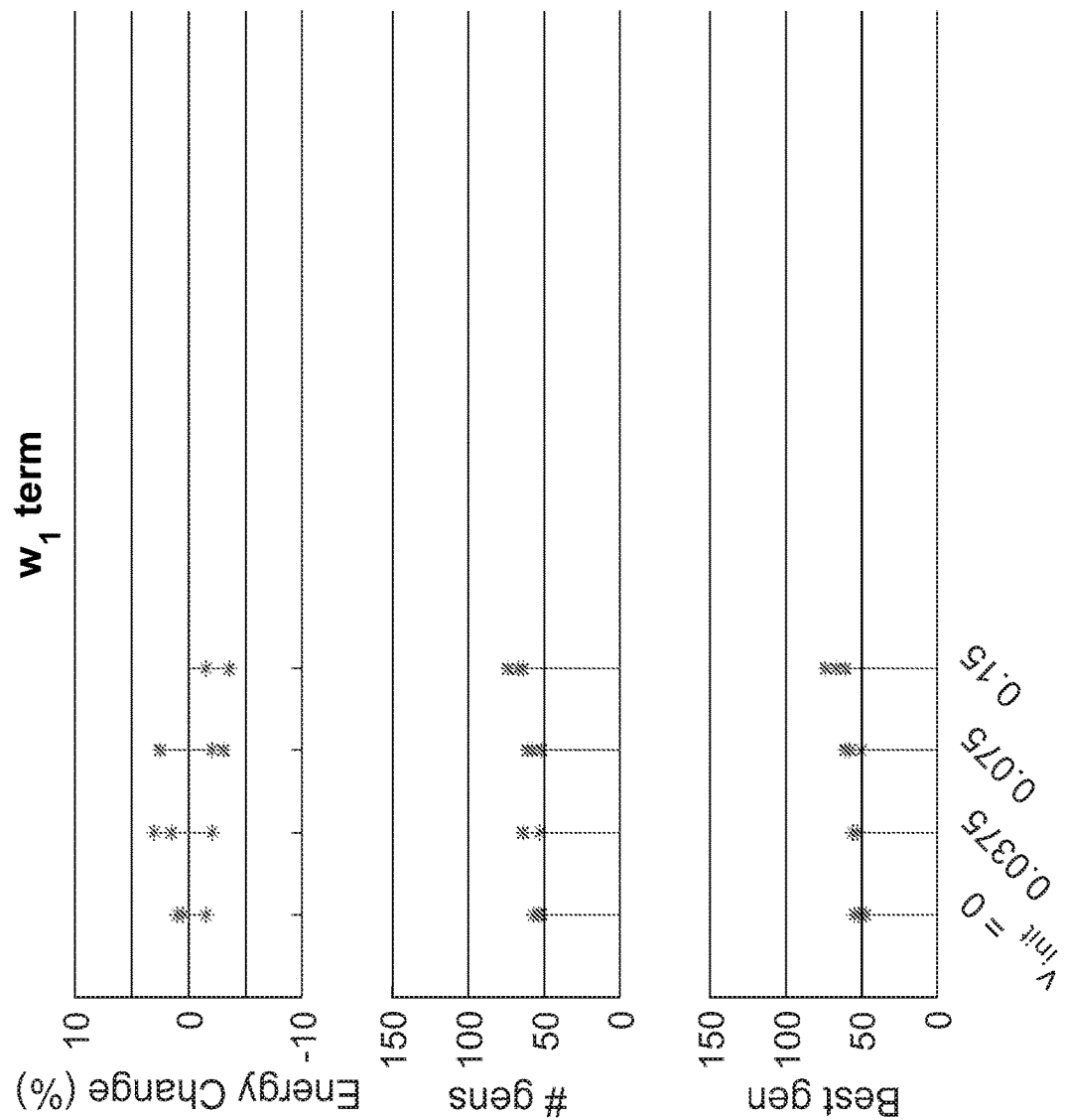
FIG. 23 includes representative data from sensitivity analyses on the addition of an exploration term to the velocity equation. Top row: Percent changes in energy referenced to the mean energy across 3 trials with the default parameters. Middle row: Total number of generations (≥50) to attain the termination criteria. Bottom row: Generation number at which the final waveform was obtained.

As shown in FIGS. 22 and 23, the addition of the exploration term with different initial target velocities had little impact on the final waveform shapes or energies, or on the rates of termination. All trials terminated based on swarm convergence.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

What is claimed is:

1. A method of identifying an optimized waveform shape for blocking neural conduction, the method comprising:
   generating a plurality of waveforms using a global optimization algorithm based on predetermined performance criteria;
   evaluating the plurality of waveforms for neuronal conduction block using a computational model of extracellular neuronal stimulation; and
   identifying at least one candidate waveform having an optimized shape capable of blocking neural conduction;
   wherein the predetermined performance criteria comprise at least one of: minimizing energy required for conduction block, minimizing power required for conduction block, minimizing charge imbalance in the optimized waveform, minimizing onset response produced when the optimized waveform is turned on, maximizing degree of conduction block, minimizing voltage required for conduction block with the optimized waveform, minimizing current required for conduction block with the optimized waveform, minimizing charge required for conduction block with the optimized waveform, maximizing therapeutic benefit produced by application of the optimized waveform, minimizing adverse effect produced by application of the optimized waveforms, maximizing selectivity of block between nerve fiber types blocked by application of the optimized waveform, maximizing selectivity of block between nerve fiber diameters blocked by application of the optimized waveform, maximizing selectivity between nerve fiber locations blocked by application of the optimized waveform, and any combinations and derivatives thereof.

2. The method of claim 1, wherein the global optimization algorithm comprises at least one of a genetic algorithm, a particle swarm algorithm, a simulated annealing algorithm, an ant colony algorithm, an estimation of distribution algorithm, and any combinations and derivations thereof.

3. The method of claim 1, wherein the predetermined performance criteria are incorporated into a cost function used to evaluate the fitness of the plurality of waveforms.

4. The method of claim 1, wherein the predetermined performance criteria comprise at least one of: minimizing energy required for conduction block, minimizing the onset response produced when the optimized waveform is turned on, maximizing selectivity of block between nerve fiber types blocked by application of the optimized waveform, and/or maximizing selectivity of block between nerve fiber diameters blocked by application of the optimized waveform.

5. The method of claim 1, wherein the computational model of extracellular neuronal stimulation is coupled to the global optimization algorithm based on the predetermined performance criteria.

6. The method of claim 1, wherein the computational model comprises at least one of: a model of an A-type myelinated axon, a model of a B-type myelinated axon, or a model of a C-type unmyelinated axon.

7. The method of claim 1, wherein the candidate waveform is monophasic, multiphasic, or biphasic.

8. The method of claim 1, wherein the candidate waveform is charge-balanced.

9. The method of claim 8, wherein a minimum energy of the candidate waveform at threshold for conduction block is from about 5% to about 200% of the energy required for conduction block with a waveform generated without using the global optimization algorithm, such as a sinusoid, a symmetric charge-balanced rectangular waveform with 100% duty cycle, or a symmetric charge-balanced rectangular waveform with 25 μs per phase.

10. The method of claim 1, wherein the candidate waveform blocks neural conduction at a waveform repetition frequency from about 1 to about 100 kHz.

11. The method of claim 1, wherein the global optimization algorithm is a particle swarm optimization (PSO) algorithm.

12. The method of claim 11, wherein:
a minimum swarm energy of the PSO algorithm varies less than about 0.1% to about 10.0% over from about 10 generations to about 100 generations after generating a minimum number of generations;
minimum and maximum waveform energies in the swarm at a given generation are less than 10% apart after generating a minimum number of generations;
or any combinations thereof.

13. A system for blocking neural conduction, the system comprising:
an electrode sized and configured for implantation in proximity to neural tissue; and
a pulse generator coupled to the electrode, the pulse generator including a power source comprising a battery and a microprocessor coupled to the battery, wherein the pulse generator is capable of applying to the electrode a waveform having an optimized shape capable of blocking neural conduction;
wherein the optimized waveform shape is optimized to meet performance criteria comprising at least one of: minimizing energy required for conduction block, minimizing power required for conduction block, minimizing charge imbalance in the optimized waveform, minimizing onset response produced when the optimized waveform is turned on, maximizing degree of conduction block, minimizing voltage required for conduction block with the optimized waveform, minimizing current required for conduction block with the optimized waveform, minimizing charge required for conduction block with the optimized waveform, maximizing therapeutic benefit produced by application of the optimized waveform, minimizing adverse effect produced by application of the optimized waveforms, maximizing selectivity of block between nerve fiber types blocked by application of the optimized waveform, maximizing selectivity of block between nerve fiber diameters blocked by application of the optimized waveform, maximizing selectivity of block between nerve fiber locations blocked by application of the optimized waveform, and any combinations and derivatives thereof.

14. The system of claim 13, wherein the waveform blocks neural conduction at a waveform repetition frequency from about 1 to about 100 kHz.

15. The system of claim 13, wherein the shape of the optimized waveform is based on a sum of sinusoidal functions, a sum of Gaussian functions, or any combinations and derivations thereof.

16. A method for blocking neural conduction using the system of claim 13, the method comprising:
programming the pulse generator to output the waveform, wherein the waveform comprises an optimized shape capable of blocking neural conduction, and wherein the optimized waveform shape is optimized to meet performance criteria comprising at least one of, minimizing energy required for conduction block, minimizing power required for conduction block, minimizing charge imbalance in the optimized waveform, minimizing onset response produced when the optimized waveform is turned on, maximizing degree of conduction block, minimizing voltage required for conduction block with the optimized waveform, minimizing current required for conduction block with the optimized waveform, minimizing charge required for conduction block with the optimized waveform, maximizing therapeutic benefit produced by application of the optimized waveform, minimizing adverse effect produced by application of the optimized waveforms, maximizing selectivity of block between nerve fiber types blocked by application of the optimized waveform, maximizing selectivity of block between nerve fiber diameters blocked by application of the optimized waveform, maximizing selectivity of block between nerve fiber locations blocked by application of the optimized waveform, and any combinations and derivatives thereof; and
setting amplitude of the waveform, wherein the waveform blocks neural conduction when delivered by the pulse generator.

17. The method of claim 16, wherein the shape of the optimized waveform is based on a sum of sinusoidal functions, a sum of Gaussian functions, or any combinations and derivations thereof.

* * * * *